United States Patent [19]
Di Fabio et al.

[11] Patent Number: 5,977,136
[45] Date of Patent: Nov. 2, 1999

[54] TETRAHYDROQUINOLINES AS NMDA ANTAGONISTS

[75] Inventors: Romano Di Fabio; Simone Giacobbe; Barbara Bertani; Fabrizio Micheli, all of Verona, Italy

[73] Assignee: Glaxo Wellcome SpA, Verona, Italy

[21] Appl. No.: 09/029,860

[22] PCT Filed: Sep. 26, 1996

[86] PCT No.: PCT/EP96/04206

§ 371 Date: Mar. 17, 1998

§ 102(e) Date: Mar. 17, 1998

[87] PCT Pub. No.: WO97/12870

PCT Pub. Date: Apr. 10, 1997

[30] Foreign Application Priority Data

Sep. 29, 1995 [GB] United Kingdom .................. 9519893
Aug. 17, 1996 [GB] United Kingdom .................. 9617306

[51] Int. Cl.$^6$ .......................... A61K 31/47; C07D 215/48

[52] U.S. Cl. ................. 514/311; 514/314; 514/235.5; 544/128; 546/165

[58] Field of Search .................................. 514/311, 314, 514/235.5; 546/165; 544/128

[56] References Cited

FOREIGN PATENT DOCUMENTS 0 386 839   9/1990   European Pat. Off. .

OTHER PUBLICATIONS

R.W. Carling et al., "Anticonvulsant Activity of Glycine–Site NMDA Antagonists", *Bioorganic & Medicinal Chemistry Letters*, vol. 3, No. 1, 1993, pp. 65–70.

*Primary Examiner*—Evelyn Mei Huang
*Attorney, Agent, or Firm*—Bacon & Thomas, PLLC

[57] ABSTRACT

Compounds of formula (I) or a salt, or metabolically labile ester thereof, processes for the preparation thereof and their use as antagonists of excitatory amino acids.

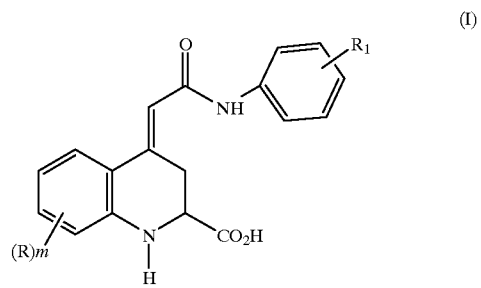

16 Claims, No Drawings

TETRAHYDROQUINOLINES AS NMDA ANTAGONISTS

This application is the national phase of PCT/EP96/04206, filed on Sep. 26, 1996, published as WO 97/12870 on Apr. 10, 1997.

This invention relates to 1,2,3,4 tetrahydroquinoline derivatives, to processes for their preparation, to pharmaceutical compositions containing them and to their use in medicine. In particular, it relates to 1,2,3,4 tetrahydroquinoline derivatives which are potent and specific antagonists of excitatory amino acids.

Carling et al, Bioorganic and Medicinal Chemistry Letters Vol 13 pp 65–70 1993 teaches 4-substituted-2-carboxy tetrahydroquinolines having good in vitro affinity for the glycine modulatory site of the NMDA receptor complex but at best only weak in vivo activity. More particularly it teaches that such derivatives substituted at the 4 position by the group $CH_2CO_2H$ or $CH_2CONHPh$ have little or no in vivo activity when administered systemically (ip).

We have found a novel group of 4 substituted 2-carboxy-tetrahydroquinoline derivatives which not only have a good in vitro affinity for the strychnine insensitive glycine binding site associated with the NMDA receptor complex but also good in vivo activity when administered intravenously (iv).

Thus the present invention provides a compound of formula (I)

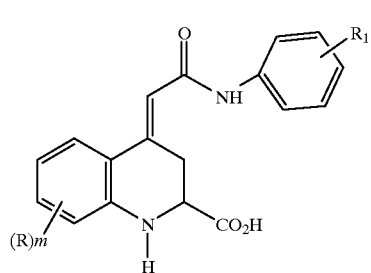

(I)

or a salt, or metabolically labile ester thereof wherein R represents a group selected from halogen, alkyl, alkoxy, amino, alkylamino, dialkylamino, hydroxy, trifluoromethyl, trifluoromethoxy, nitro, cyano, $SO_2R_2$ or $COR_2$ wherein $R_2$ represents hydroxy, methoxy, amino, alkylamino or dialkylamino; m is zero or an integer 1 or 2;

$R_1$ represents hydrogen, alkyl, alkoxy, nitro, trifluoromethyl, halogen or $(CH_2)_nR_3$ wherein $R_3$ is hydroxy, $COR_4$, $NR_5R_6$, $NHCOR_7$, or $NHCONR_8R_9$ group.

$R_4$ represents an alkoxy, amino or hydroxyl group;

$R_5$ and $R_6$ each independently represent hydrogen or alkyl group or $R_5$ and $R_6$ together with the nitrogen atom to which they are attached represent a heterocyclic group;

$R_7$ represents a hydrogen atom or optionally substituted alkyl, alkoxy, aryl or heterocyclic group;

$R_8$ represents hydrogen or alkyl group;

$R_9$ represents hydrogen, optionally substituted alkyl, aryl, heterocyclic or cycloalkyl group;

n is zero or an integer from 1 to 4.

In compounds of formula (I) the exocyclic double bond is in the trans (E) configuration.

For use in medicine the salts of the compounds of formula (I) will be physiologically acceptable thereof. Other salts however may be useful in the preparation of the compounds of formula (I) or physiologically acceptable salts thereof. Therefore, unless otherwise stated, references to salts include both physiologically acceptable salts and non-physiologically acceptable salts of compounds of formula (I).

Suitable physiologically acceptable salts of compounds of the invention include base addition salts and where appropriate acid addition salts. Suitable physiologically acceptable base addition salts of compounds of formula (I) include alkali metal or alkaline metal salts such as sodium, potassium, calcium, and magnesium, and ammonium salts, formed with amino acids (e.g. lysine and arginine) and organic bases (e.g. procaine, phenylbenzylamine, ethanolamine diethanolamine and N-methyl glucosamine).

The compounds of formula (I) and/or salts thereof may form solvates (e.g. hydrates) and the invention includes all such solvates.

Compounds of formula (I) and in particular the base addition salts thereof e.g. sodium salt have been found to have an advantageous profile of solubility in water.

The term alkyl as used herein as a group or part of a group refers to a straight or branched chain alkyl group containing from 1 to 4 carbon atom examples of such groups including methyl, ethyl, propyl, isopropyl, n-butyl, isobutyl, secondary butyl or tertiary butyl.

The term optionally substituted alkyl as used herein refers to an alkyl group as defined above and which is substituted by one or more hydroxy. carboxyl, and amino groups.

The term halogen refers to a fluorine, chlorine, bromine or iodine atom.

The term aryl refers to an optionally substituted phenyl group or a 5 or 6 membered heteroaryl in which the 5-membered heteroaryl group contains 1 or 2 heteroatoms selected from oxygen sulphur or nitrogen and 6-membered heteroaryl group containing 1 or 2 nitrogen atoms.

Examples of suitable heteroaryl groups include furanyl, thiophenyl, imidazolyl, thiazolyl, oxazolyl, pyridinyl, and pyrimidinyl.

The term optionally substituted phenyl refers to a phenyl group substituted with up to 3 substituents selected from halogen, C1–4 alkyl, C1–4 alkoxy, amino, alkylamino, hydroxy, trifluoromethyl, carboxyl or methoxycarbonyl.

The term cycloalkyl refers to a $C_{3-7}$cycloalkyl group which may optionally be substituted or 1 or 2 $C_{1-4}$ alkyl groups e.g. cyclopropyl, cyclobutyl, cyclopentyl, cyclohexyl cycloheptyl or 2-methylcyclohexyl.

The term optionally substituted heterocyclic group refers to 5–7 membered saturated heterocyclic groups containing one or two heteroatoms selected from oxygen, sulphur or nitrogen. Examples of suitable groups containing a single heteroatom include tetrahydropyranyl e.g. 4-tetrahydropyranyl, pyrrolidinyl e.g. 2 or 3 pyrrolidinyl, piperidinyl e.g. 4- or 3-piperidinyl and N-substituted derivatives therefore (e.g. N-alkyl such as e.g. methyl or N-acyl such as N-alkanoyl e.g. acetyl or N-alkoxycarbonyl e.g. ethoxycarbonyl), piperidino or pyrrolidino. Examples of suitable groups containing 2 heteroatoms include morpholino, thiomophlino or piperazino.

When $R_5$ and $R_6$ together with the nitrogen atom to which they are attached represent an heterocyclic group this is a saturated 5–7 membered ring optionally containing an additional heteroatom selected from oxygen, sulphur or nitrogen.

Examples of such groups include morpholino, 2,6 dimethylmorpholino, piperidino, pyrrolidino, piperazino or N-methylpiperazino.

The compounds of formula(I) possess at least one asymmetric carbon atom (namely the carbon atom occupying the 2 position of the 1, 2, 3, 4 tetrahydroquinoline ring system)

and other asymmetric carbon atoms are possible in the groups R and $R_1$. It is to be understood that all enantiomers and diastereaisomers and mixtures thereof are encompassed within the scope of the present invention.

It will be appreciated that the compounds of formula (I) may be produced in vivo by metabolism of a suitable prodrug. Such prodrugs include for example physiologically acceptable metabolically labile esters of compounds of the general formula (I). These may be formed by esterification, for example of any of the carboxylic acid groups in the parent compound of general formula (I) with, where appropriate, prior protection of any other reactive groups present in the molecule, followed by deprotection if required. Examples of such metabolically labile esters include $C_{1-4}$alkyl esters e.g. methyl or ethyl esters, substituted or unsubstituted aminoalkyl esters (e.g. aminoethyl, 2-(N,N-diethylamino) ethyl, or 2-(4-morpholino)ethyl esters or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-(1-methoxy-1-methyl) ethylcarbonyloxyethyl, 1-benzoyloxyethyl, isopropoxycarbonyloxymethyl, 1-isopropoxycarbonyloxyethyl, cyclohexyl carbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxy)carbonyloxyethyl or 1-(4-tetrahydropyranyl)carbonyloxyethyl.

For compounds of formula (I) m is conveniently 1 or 2 and within these compounds those wherein R is at the 5 and/or 7 position are preferred.

The group R is conveniently a halogen atom, such as bromine or chlorine and preferably is a chlorine atom.

The substituent $R_1$ may be in the 2, 3 or 4 position in the phenyl ring. Conveniently $R_1$ is at the 3 or 4 position and is preferably at the 4 position. When $R_1$ is the group $(CH_2)_nR_3$ n is conveniently zero, 1 or 2.

Examples of suitable $R_1$ group include hydrogen, halogen e.g. chlorine, alkoxy e.g. methoxy, $(CH_2)_nCOR_4$ wherein $R_4$ is amino or hydroxyl, $(CH_2)_nNR_5R_6$ in which $R_5$ is hydrogen and $R_6$ is hydrogen or alkyl e.g. methyl, ethyl, or $NR_5R_6$ represents a saturated 6 membered ring containing oxygen e.g. morpholino, $(CH_2)_nNHCOR_7$ wherein $R_7$ is hydrogen, alkyl e.g. methyl, isopropyl, isobutyl, aryl group e.g. phenyl or pyridyl e.g. 3-pyridyl or $(CH_2)_nNHCONHR_9$ wherein $R_9$ is hydrogen, phenyl (optionally substituted with methoxy), heterocyclic e.g. 4-tetrahydropyranyl or cycloalkyl e.g. cyclopropyl or cyclohexyl. Within these groups of compounds n is conveniently zero 1 or 2.

A preferred group of compounds of formula (I) are those wherein m is 2 and R which is at the 5 and 7 position is bromine or more particularly chlorine. A further preferred group of compounds of formula (I) are those wherein $R_1$ is hydrogen, chlorine, $(CH_2)_nCOR_4$ wherein $R_4$ is hydroxyl or amino and n is zero, 1 or 2, e.g. carboxymethyl or carbamoylmethyl, $(CH_2)_nNR_5R_6$ wherein $R_5$ and $R_6$ are each hydrogen or $NR_5R_6$ represents a morpholino group and n is zero 1 or 2 e.g. amino or morpholinomethyl $(CH_2)_n$NHCOR7 wherein $R_7$ is hydrogen or $C_{1-4}$alkyl e.g. methyl, isopropyl or isobutyl, n is zero 1 or 2 e.g. acetamido, acetamidoethyl, acetamidoethyl, formamidomethyl, isobutyrylamino, isobutyrylaminomethyl, isobutyrylaminoethyl, 3-methylbutyrylaminomethyl, $(CH_2)_n$NHCONH$_2$ wherein n is zero, 1 or 2 e.g. ureidomethyl:

Specific preferred compounds of the invention include:
(±) (E) 4-(acetylamino-phenylcarbamoylmethylene)-5,7-dichloro-1,2,3,4-tetrahydroquinoline-2-carboxylic acid, (±) (E) 5,7-Dichloro-4-phenylcarbamoylmethylene-1,2,3,4-tetrahydro-quinoline-2-carboxylic acid, (±) (E) 7-Chloro-4-phenylcarbamoylmethylene-1,2,3,4-tetrahydro-quinoline-2-carboxylic acid, (±) (E) 5,7-Dibromo-4-phenylcarbamoylmethylene-1,2,3,4-tetrahydro-quinoline-2-carboxylic acid, (±) (E) 4-(4-Amino-phenylcarbamoylmethylene)-5,7-dichloro-1,2,3,4-tetrahydro-quinoline-2-carboxylic acid, (±) (E) 4-(3-Acetylamino-phenylcarbamoylmethylene)-5,7-dichloro-1,2,3,4-tetrahydro-quinoline-2-carboxylic acid, (±) (E) 5,7-Dichloro-4-(4-isobutyrylamino-phenylcarbamoylmethylene)-1,2,3,4-tetrahydro-quinoline-2-carboxylic acid, (±) (E) 5,7-Dichloro-4-[4-(3-methyl-butyrylamino)-phenylcarbamoylmethylene]-1,2,3,4-tetrahydro-quinoline-2-carboxylic acid (±) (E) 5,7-Dichloro-4-(3-chloro-phenylcarbamoylmethylene)-1,2,3,4-tetrahydro-quinoline-2-carboxylic acid, (±) (E) 5,7-Dichloro-4-[4-(isobutyrylamino-methyl)-phenylcarbamoylmethylene]-1,2,3,4-tetrahydro-quinoline-2-carboxylic acid (±) (E) 5,7-Dichloro-4-[4-(ureidomethyl)-phenylcarbamoylmethylene]-1,2,3,4-tetrahydro-quinoline-2-carboxylic acid, (±) (E) 4-[4-(Acetylamino-methyl)-phenylcarbamoylmethylene]-5,7-dichloro-1,2,3,4-tetrahydro-quinoline-2-carboxylic acid, (±) (E) 5,7-Dichloro-4-(4-formylaminomethyl-phenylcarbamoylmethylene)-1,2,3,4-tetrahydro-quinoline-2-carboxylic acid, (±) (E) 5,7-Dichloro-4-(4-morpholin-4-ylmethyl-phenylcarbamoylmethylene)-1,2,3,4-tetrahydro-quinoline-2-carboxylic acid (±) (E) 4-[4-(2-Acetylamino-ethyl)-phenylcarbamoylmethylene]-5,7-dichloro-1,2,3,4-tetrahydro-quinoline-2-carboxylic acid, (±) (E) 5,7-Dichloro-4-[4-(2-isobutyrylamino-ethyl)-phenylcarbamoylmethylene]-1,2,3,4-tetrahydro-quinoline-2-carboxylic acid (±) (E) 4-(4-Carbamoylmethyl-phenylcarbamoylmethylene)-5,7-dichloro-1,2,3,4-tetrahydro-quinoline-2-carboxylic acid, (±) (E) 4-(4-Carboxymethyl-phenylcarbamoylmethylene)-5,7-dichloro-1,2,3,4-tetrahydro-quinoline-2-carboxylic acid, and physiologically acceptable salts e.g. sodium salt or metabolically labile esters thereof.

The compounds of formula (I) and/or physiologically acceptable salts thereof are excitatory amino acid antagonists. More particularly they are potent antagonists at the strychnine insensitive glycine binding site associated with the NMDA receptor complex. As such they are potent antagonists of the NMDA receptor complex. These compounds are therefore useful in the treatment or prevention of neurotoxic damage or neurodegenerative diseases. Thus the compounds are useful for the treatment of neurotoxic injury which follows cerebral stroke, thromboembolic stroke, hemorrhagic stroke, cerebral ischemia, cerebral vasospam, hypoglycemia, anaesia, hypoxia, anoxia, perinatal asphyxia cardiac arrest. The compounds are useful in the treatment of chronic neurodegenerative diseases such as; Huntingdon's disease, Alzheimer's senile dementia, amyotrophic lateral sclerosis, Glutaric Acidaemia type, multi-infarct dementia, status epilecticus, contusive injuries (e.g. spinal cord injury and head injury), viral infection induced neurodegeration (e.g. AIDS, encephalopaties), Down syndrome, epilepsy, schizophrenia, depression, anxiety, pain, neurogenic bladder, irritative bladder disturbances, drug dependency, including withdrawal symptoms from alcohol, cocaine, opiates, nicotine, benzodiazepine, and emesis.

The potent and selective action of the compound of the invention at the strychnine-insensitive glycine binding site present on the NMDA receptor complex may be readily determined using conventional test procedures. Thus the ability to bind at the strychnine insensitive glycine binding site was determined using the procedure of Kishimoto H et al. J Neurochem 1981, 37 1015–1024. The selectivity of the action of compounds of the invention for the strychnine insensitive glycine site was confirmed in studies at other ionotropic known excitatory amino acid receptors. Thus compounds of the invention were found to show little or no affinity for the kainic acid (kainate) receptor, a-amino-3-hydroxy-5-methyl-4-isoxazole-proprionic acid (AMPA) receptor or at the NMDA binding site.

Compounds of the invention have also been found to inhibit NMDA induced convulsions in mice using the procedure Chiamulera C et al. Psychopharmacology (1990) 102, 551–552.

The invention therefore provides for the use of a compound of formula (I) and/or physiologically acceptable salt or metabolically labile ester thereof for use in therapy and in particular use as medicine for antagonising the effects of excitatory amino acids upon the NMDA receptor complex.

The invention also provides for the use of a compound of formula (I) and/or a physiologically acceptable salt or metabolically labile ester thereof for the manufacture of a medicament for antagonising the effects of excitatory amino acids upon the NMDA receptor complex.

According to a further aspects the invention also provides for a method for antagonising the effects of excitatory amino acids upon the NMDA receptor complex, comprising administering to a patient in need thereof an antagonistic amount of a compound of formula (I) and/or a physiologically acceptable salt or metabolically labile ester thereof.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated, the route of administration and the age and the condition of the patient and will be ultimately at the discretion of the attendant physician. In general however doses employed for adult human treatment will typically be in the range of 2 to 800 mg per day, dependent upon the route of administration.

Thus for parenteral administration a daily dose will typically be in the range 20–100 mg, preferably 60–80 mg per day. For oral administration a daily dose will typically be within the range 200–800 mg, e.g. 400–600 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical, it is preferable to present the active ingredient as a pharmaceutical formulation.

The invention thus further provides a pharmaceutical formulation comprising a compound of formula (I) or a pharmaceutically acceptable salt or metabolically labile ester thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant, or rectal administration. Parenteral administration is preferred.

Tablets and capsules for oral administration may contain conventional excipients such as binding agents, for example, syrup, accacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs, with the use of a suitable propellant, such as dichlorodifluoromethane, tirchlorofluoromethane, dichloro-tetrafluoroethane, carbon dioxide or other suitable propellants, such as dichlorodifluoromethane, trichlorofluoromethane, dichloro-tetrafluoroethane, carbon dioxide or other suitable gases, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable carrier such as lactose or starch. The powder composition may be presented in unit dosage form in, for example, capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramuscularly) or by intramuscular injection Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups R, m, $R_1$ are as defined for the compounds of formula (I) unless otherwise stated.

Compounds of formula (I) may be prepared by the cyclisation of a compound of formula (II) in which $R_{10}$ is a carboxylic protecting group, $R_{11}$ represents a bromine or iodine atom, $R_{12}$ represents hydrogen or a nitrogen protecting group and $R_1$ has the meanings defined in formula(I) or a protected derivative thereof,

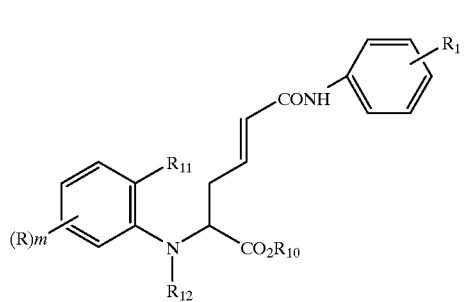

(II)

followed where necessary or desired by removal of one or more protecting groups.

In one embodiment of this process the reaction may be carried out using a catalytic amount of a Palladium (O) complex such as tetrakis(triphenylphosphine)palladium and a suitable organic base such as trialkylamine e.g. triethylamine or inorganic base, e.g. potassium carbonate. The reaction is conveniently carried out in an aprotic solvent such as acetonitrile or dimethylformamide at a temperature with the range of 60° C. to 150° C. followed, where necessary or desired, by subsequent removal of the carboxyl protecting group $R_{10}$ and any protecting group $R_{12}$.

In a further embodiment of the process the reaction is carried out using a catalytic amount of a Pd(II) salt such as: palladium acetate, in the presence of a siutable organic base such as trialkyl amine e.g. triethylamine and of a triarylphosphine such as triphenylphosphine.

The reaction is carried out in an aprotic solvent such as acetonitrile or dimethylformamide and preferably with heating, where necessary or desired, by subsequent removal of the carboxyl protecting group $R_{10}$ and any protecting group $R_{12}$.

Suitable carboxyl protecting groups $R_{10}$ for use in this reaction include alkyl, trichloroalkyl, trialkylsilylalkyl, or arylmethyl groups such as benzyl, nitrobenzyl or trityl.

When $R_{12}$ is nitrogen protecting examples of suitable groups include alkoxycarbonyl e.g. t-butoxycarbonyl, arylsulphonyl e.g. phenysulphonyl or 2-trimethylsilylethoxymethyl.

In a further process of the invention compounds of formula(I), may be prepared by reaction of an activated derivative of the carboxylic acid (III) in which $R_{10}$ is a carboxyl protecting group and $R_{12}$ is hydrogen or a nitrogen protecting group as defined in formula (II)

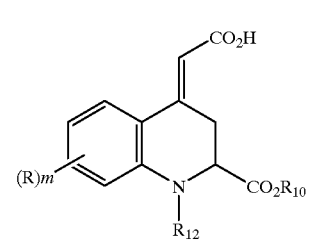

(III)

with the amine(IV)

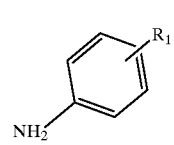

(IV)

wherein R1 has the meaning defined in formula(I) or a protected derivative thereof, followed where necessary by subsequent removal of the carboxyl protecting group $R_{10}$ and any nitrogen protecting group $R_{12}$.

Suitable activated derivatives of the carboxyl group include the corresponding acyl halide, mixed anhydride, activated ester such as a thioester or the derivative formed between the carboxylic acid group and a coupling agent such as that used in peptide chemistry, for example carbonyl diimidazole or a diimide such as dicyclohexylcarbodiimide.

The reaction is preferably carried out in an aprotic solvent such as a hydrocarbon, a halohydrocarbon, such as dichloromethane or an ether such as tetrahydrofuran.

Suitable carboxyl protecting groups $R_{10}$ for use in this reaction include alkyl, trichloroalkyl, trialkylsilylalkyl, or arylmethyl groups such as benzyl, nitrobenzyl or trityl.

When $R_{12}$ is nitrogen protecting examples of suitable groups include alkoxycarbonyl e.g. t-butoxycarbonyl, arylsulphonyl e.g. phenysulphonyl or 2-trimethylsilylethoxymethyl The activated derivatives of the carboxylic acid (III) may be prepared by conventional means. A particularly suitable activated derivative for use in this reaction is thioester such as that derived from pyridine-2-thiol. These esters may conveniently be prepared by treating the carboxylic acid (III) with 2,2'-dithiopyridine and triphenylphosphine in a suitable aprotic solvent such as an ether e.g. tetrahydrofuran, a halohydrocarbon e.g. dichloromethane, an amide e.g. N,N-dimethylformamide or acetonitrile.

Compounds of formula (I) wherein $R_1$ is $(CH_2)_n NHCOR_7$ in which $R_7$ has the meaning defined in formula(I) may be also prepared by reaction of the amine (V) wherein (R),m, $R_{12}$ and $R_{10}$ have the meanings defined in formula(I)

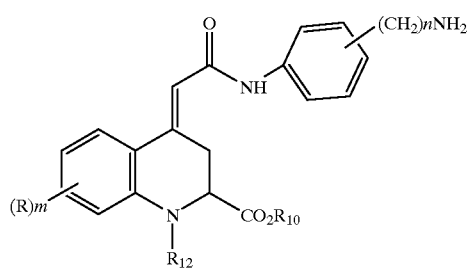

(V)

with an activated derivative of the acid $R_7CO_2H$ wherein $R_7$ has the meaning defined in formula(I) or is protected derivatives thereof, followed where appropriate by removal of any protecting groups.

Suitable activated derivatives of the acid $R_7CO_2H$ include the corresponding acyl halides e.g. acyl chlorides. The reaction is conveniently carried out in an aprotic solvent such as ether e.g. tetrahydrofuran and in the presence of a base such as tertiary amine e.g. trietylamine.

Compounds of formula(I) wherein $R_1$ is $(CH_2)_n NHCONR_8R_9$ group in which $R_8$ and $R_9$ have the meanings defined in formula(I) may be also prepared by reaction of the amine derivative of formula(V) with an isocyanate of formula(VI) wherein $R_8$ and $R_9$ have the meaning defined in formula(I) or are protected derivatives therof or with the compound(VII) wherein $R_8$ and $R_9$ have the meanings defined in formula(I) or are protected derivatives therof and $R_{13}$ is optionally substituted phenoxy, halogen or imidazole group followed where necessary or desired by removal of any protecting group.

(VI)

(VII)

The reaction with the compound(VI) is conveniently carried out in a solvent such as tetrahydrofuran or aqueous tetrahydrofuran, a halohydrocarbon (e.g. dicholoromethane) or acetonitrile optionally in the presence of a base such as triethylamine, and at a temperature with the range of 0–80° C.

The reaction with the compound(VII) is preferably carried out in a solvent such as halohydrocarbon (e.g. dichloromethane) or an ether (e.g. tetrahydrofuran) or an amide (e.g. N,N-dimethylformamide) at a temperature with the range of room temperature to the reflux temperature of the sovent and optionally in the presence of a base such as tertiary amine e.g. triethylamine. When the reaction is carried out using a compound of formula(VII) wherein $R_{13}$ is halogen the reaction is conveniently carried out at a temperature with the range 0–60° C.

Suitable carboxyl protecting groups $R_{10}$ for use in this reaction include alkyl, trichloroalkyl, trialkylsilylalkyl, or arylmethyl groups such as benzyl, nitrobenzyl or trityl.

When $R_{12}$ is nitrogen protecting examples of suitable groups include alkoxycarbonyl e.g. t-butoxycarbonyl, arylsulphonyl e.g. phenysulphonyl or 2-trimethylsilylethoxymethyl Compounds of formula (II) may be prepared from compound of formula (VIII) in which $R_{10}$ is a carboxyl protecting group and $R_{12}$ is hydrogen or a nitrogen protecting group as defined in formula (II) and $R_{11}$ represents a bromine or iodine atom

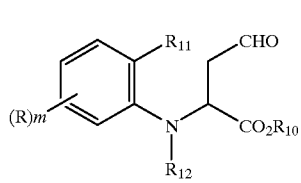

(VIII)

by rection with an appropriate phosphorus reagent capable of converting the group CHO into the group:

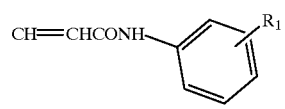

followed, where necessary or desired, by removal of the carboxyl protecting group $R_{10}$ and nitrogen protecting group $R_{12}$ In one embodiment of this process the reaction may be carried out using a phoshorus ylide of formula (IX)

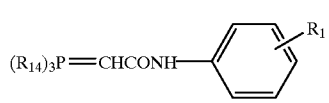

(IX)

wherein $R_{14}$ is an alkyl or phenyl group and $R_1$ has the meanings defined in formula(I) or a protected derivative thereof.

The reaction is carried out in an aprotic solvent such as acetonitrile or dimethylformamide at a temperature ranging from $-10°$ C. to the reflux temperature of the solvent.

Compounds of formula (VIII) may be prepared by ozonization of the allyl compound of formula(X) in which $R_{10}$ is a carboxyl protecting group, $R_{12}$ is hydrogen or a nitrogen protecting group as defined above and $R_{11}$ represents a bromine or iodine atom.

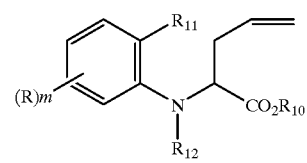

(X)

The reaction may be effected by passing a stream of ozone into a solution of compound of formula (X) in the presence of dimethyl sulphide or triphenylphosphine in a suitable solvent such as halohydrocarbon e.g. dichloromethane at low temperature e.g. $-78°$ C.

Compounds of formula (X) wherein $R_{12}$ is hydrogen atom and $R_{10}$ is carboxyl protecting group as defined above may be prepared by reaction of the amine(XI) wherein $R_{11}$ represents a bromine or iodine atom with the aldehyde (XII) in which $R_{10}$ is carboxyl protecting group

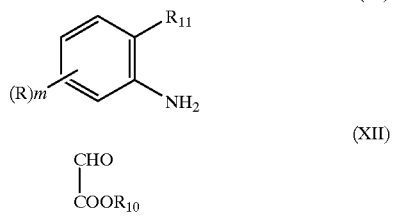

followed by addition of allyltributyltin in the presence of Lewis acid such as titanium(IV) chloride or boron trifluoride etherate. The reaction conveniently takes place in a solvent such as hydrocarbon e.g. toluene or halogenated hydrocarbon e.g. dichloromethane at a temperature ranging from −78° C. to room temperature.

Compounds of formula (X) in which $R_{12}$ is nitrogen protecting group and $R_{10}$ is carboxyl protecting group as defined above may be prepared from the compound of formula(X) wherein $R_{12}$ represents hydrogen atom using conventional procedure for preparing such protected nitrogen atom.

Compounds of formula (III) may be prepared by the cyclisation of a compound of formula (XIII) in which $R_{10}$ is a carboxylic protecting group, $R_{11}$ represents a bromine or iodine atom, $R_{12}$ represents hydrogen or a nitrogen protecting group as defined above, and $R_{15}$ represents a suitable carboxyl protecting group such as t butyl group

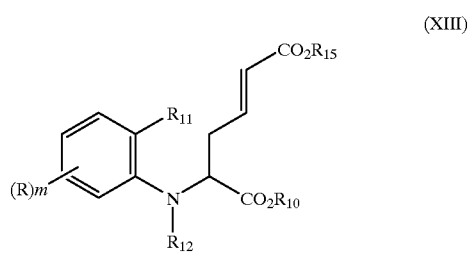

using similar reaction conditions for those described above for the cyclisation of compounds of formula (II), followed by removal of the carboxyl protecting group $R_{15}$ and where necessary or desired by removal of the nitrogen protecting group $R_{12}$ Compounds of formula (XIII) may be prepared from compound of formula(VIII) and a phosphourus ylide ($R_{14}$)$_3$P=CHCO$_2$R$_{15}$ in which $R_{14}$ has the meaning defined in formula (IX) and $R_{15}$ is defined above, using similar reaction condition for those described above for the reaction of (VIII) with compound of formula (IX).

Compounds of formula (V) may be prepared by any of the processes described by the general procedures described above for preparing compounds of formula (I) using the appropriate intermediates (II), (IV), (IX)

Compounds of formula (IV), (VI), (VII) (IX), (XI) and (XII) are either known compounds or may be prepared by analogous methods to those used for known compounds.

In any of the above reactions the carboxyl protecting group may be removed by conventional procedures known for removing such groups. Thus compounds where $R_{10}$ is a benzyl group, this may be removed by hydrolysis using an alkali metal hydroxide e.g. lithium hydroxide or sodium hydroxide in a suitable solvent such as ethanol or isopropanol, water or mixtures thereof, followed, where desired or necessary, by that addition of a suitable acid e.g. hydrochloric acid to give the corresponding free carboxylic acid.

In any of the above reactions the nitrogen protecting group may be removed by conventional procedures known for removing such groups, for example by acid or base hydrolysis. Thus when $R_{12}$ is alkoxycarbonyl e.g. t-butoxycarbonyl or phenylsulphonyl it may be removed by alkaline hydrolysis using for example lithium hydroxide in a suitable solvent such as tetrahydrofuran or an alkanol e.g. isopropanol. Alternatively the alkoxycarbonyl group may be removed by acid hydrolysis. When $R_{15}$ is t butyl group this may be removed by hydrolysis using organic acids e.g. formic acid.

Physiologically acceptable salts of compounds of formula (I) may be prepared by treating the corresponding acid with an appropriate base in a suitable solvent. For example alkali and alkaline metal salts may be prepared from an alkali or alkaline metal hydroxide, or the corresponding carbonate or bicarbonate thereof. Alternatively alkali or alkaline metal salts may be prepared by direct hydrolysis of carboxyl protected derivatives of compounds of formula (I) with the appropriate alkali or alkaline metal hydroxide.

Metabolically labile esters of compounds of formula (I) may be prepared by esterification of the carboxylic acid group or a salt thereof or by trans esterfication using conventional procedures. Thus, for example, acyloxyalkyl esters may be prepared by reacting the free carboxylic acid or a salt thereof with the appropriate acyloxylalkyl halide in a suitable solvent such as dimethylformamide. For the esterifcation of the free carboxyl group this reaction is preferably carried out in the presence of a quaternary ammonium halide such as tetrabutylammonium chloride or benzyltriethylammonium chloride.

Aminoalkyl esters may be prepared by transesterification of a corresponding alkyl ester e.g. methyl or ethyl ester by reaction with the corresponding aminoalkanol at an elevated temperature e.g. 50–150°.

In order that the invention may be more fully understood the following examples are given by way of illustration only.

In the Intermediates and Examples unless otherwise stated:

Melting points (m.p.) were determined on a Gallenkamp m.p. apparatus and are uncorrected. All temperatures refers to °C. Infrared spectra were measured on a FT-IR instrument. Proton Magnetic Resonance ($^1$H-NMR) spectra were recorded at 400 MHz, chemical shifts are reported in ppm downfield (d) from Me$_4$Si, used as internal standard, and are assigned as singlets (s), doublets (d), doublets of doublets (dd), triplets (t), quartets (q) or multiplets (m). Column chromathography was carrier out over silica gel (Merck AG Darmstaadt, Germany). The following abbreviations are used in text: EA=ethyl acetate, CH=cyclohexane, DCM=dichloromethane, THF=tetrahydrofuran, TFA=trifluoroacetic acid, TEA=triethylamine, PPA=polyphosphoric acid, DBU=1,8-diazobicyclo [5,4,0]undec-7-ene, DMSO=dimethylsulphoxide, Tlc refers to thin layer chromatography on silica plates. Solution were dried over anhydrous sodium sulphate; r.t. (RT) refers to room temperature.

INTERMEDIATE 1

4-Chloro-1-Iodo-2-Nitrobenzene

To a suspension of 4-chloro-2-nitroaniline (5.18 g) in a 12 N sulphuric acid solution (60 ml) cooled to 10° a solution of sodium nitrite (2.76 g) in sulphuric acid (20 ml) and polyphosphoric acid (40 ml) were sequentially added. The reaction mixture was stirred for 3 hrs at r.t., then poured into crushed ice and urea was added until gas evolution ceases.

The resulting solution was treated with an aqueous solution (20 ml) of potassium iodide (7.47 g) and heated at 70° for 1 h. The mixture was diluted with brine and extracted with EA then the organic phase was washed with brine, dried and concentrated in vacuo. The residue was purified by flash column chromatography (CH/EA=100/0 to 95/5 as eluant), obtaining the title compound as yellow solid (7.96 g). m.p. 55–56° C.

$^1$H-NMR (CDCl$_3$): 7.98 (1H, d); 7.80 (1H, d); 7.28 (1H, dd).

IR (neat): $v_{max}$ (cm$^{-1}$)=1535 (NO$_2$); 1354 (NO$_2$).

INTERMEDIATE 2

5-Chloro-2-Iodo-Aniline

To a solution of intermediate 1 (3.71 g) in 95% ethanol (25 ml) acetic acid (25 ml) and iron (2.98 g) were added. The reaction mixture was heated at 100° for 1 hr. then poured into brine, and sodium hydrogencarbonate powder was added until pH=10. After extraction with EA, the organic phase was washed with brine, dried and evaporated, affording the title compound as yellow oil (3.60 g).

$^1$H-NMR (CDCl$_3$): 7.5 (1H, d); 6.7 (1H, d); 6.5 (1H, dd); 4.2 (2H, bs).

IR (neat): $v_{max}$ (cm$^{-1}$)=3468 (NH2); 3371 (NH2); 1610 (C=C).

INTERMEDIATE 3

(+/-) 2-(5-Chloro-2-Iodo-Phenylamino)-Pent-4-Enoic Acid Benzyl Ester

To a solution of intermediate 2 (1.05 g) in dry toluene (15 ml) benzylglyoxylate (750 mg) and Na$_2$SO$_4$ (2 g) were added. The mixture was refluxed overnight. After filtration the resulting solution was concentrated under vacuum to a brown oil, which was then taken up with dichloromethane (30 ml). After cooling to −78°, TiCl$_4$ (0.46 ml) was slowly added with a syringe and stirring continued for 5 min. The solution was then allowed to warm to room temperature over 30 min by removing the dry ice/acetone bath, then cooled again to −78° and tributylallyltin (2.6 ml) added. After 1 hour the reaction was stopped by pouring it into a saturated solution of NH$_4$Cl (100 ml). The aqueous phase was extracted with EA (2×150 ml) and the combined organic fractions washed with HCl (3 N, 2×50 ml) and brine (50 ml) and dried. Final purification by column chromatography (CH/EA 95/15) gave the title compound (1.4 g) as a colorless oil.

$^1$H NMR d (CDCl$_3$) 7.55 (d, 1H), 7.34 (m, 5H), 6.47 (dd, 1H), 6.42 (d, 1H), 5.73 (m, 1H), 5.19 (m, 4H), 4.82 (d, 1H), 4.17 (m, 1H), 2.65 (m, 2H).

INTERMEDIATE 4

(+/-) 2-(5-Chloro-2-Iodo-Phenylamino)-4-Oxo-Butyric Acid Benzyl Ester

Intermediate 3 (1.43 g) was dissolved in dry dichloromethane and the resulting solution cooled to −78° with a dry ice/acetone bath. Ozone was bubbled through it until a brick-red color appeared (approx 10 min), then triphenylphosphine (0.92 g) was added and the cooling bath removed. After the warm-up was complete the solution was concentrated to dryness on the rotary evaporator and finally purified by column chromatography (CH/EA 85/25) to give the title compound (0.86 g) as a colorless oil.

$^1$H NMR:d (CDCl$_3$) 9.77 (t, 1H), 7.57 (d, 1H), 7.37 (m, 5H), 6.54 (d, 1H), 6.51 (dd, 1H), 5.20 (s, 2H), 4.99 (d, 1H), 4.52 (m, 1H), 3.07 (m, 2H).

IR: (CDCl$_3$) n$_{max}$ (cm$^{-1}$) 1730.

INTERMEDIATE 5

(+/-)(E)7-Chloro-4-Phenylcarbamoylmethylene-1,2,3,4-Tetrahydroquinoline-2-Carboxylic Acid Benzyl Ester To a solution of intermediate 4 (0.185 g) in dry acetonitrile (10 ml) and cooled to −10° phenylcarbomoylmethyl triphenylphosphonium bromide (0.241 g) and DBU (0.08 ml) were added with stirring. A white precipitate immediately formed: after 1 hour it was isolated by filtration, washed with small amounts of cold acetonitrile and dried under vacuum to give the crude(+/-)(E)2-(5-Chloro-2-iodo-phenylamino)-5-phenylcarbamoyl-pent4-enoic acid benzyl ester (0.156 g) which was dissolved in dry acetonitrile (20 ml) and the solution deoxygenated by bubbling through it dry N$_2$. To this solution, tetrakis(triphenylphosphine)palladium(0.032 g) and triethylamine (0.08 ml) were added and the reaction vessel sealed and heated to 80° for 2 hours. The brown mixture was then cooled, diluted with EA (100 ml) and washed with a saturated solution of NH$_4$Cl (50 ml). After drying with brine and with Na$_2$SO$_4$ the crude product was purified by column chromatography (CH/EA 4/1 to 3/1) to give the title compound (0.035 g) as a white solid.

$^1$H NMR: d (CDCl$_3$) 10.03 (bs, 1H), 7.64 (m, 4H), 7.38 (d, 1H), 7.30 (m, 2H), 7.22 (m, 5H), 7.03 (m, 1H), 7.03 (m, 1H), 6.96 (bd, 1H), 6.78 (d, 1H), 6.61 (dd, 1H), 6.49 (s, 1H), 5.05 (m, 2H), 4.28 (m, 1H), 4.15 (dd, 1H), 3.02 (m, 1H).

IR: (nujol) n$_{max}$ (cm$^{-1}$) 3385–3287, 1720–1645, 1599

INTERMEDIATE 6

4,6-Chloro-1-Iodo-2-Nitrobenzene

2-Nitro-4,6-dichloroaniline (5 g) was dissolved in a 12 N solution of H$_2$SO$_4$ (20 ml) and cooled at 0°. Then, a solution of NaNO$_2$ (2.15 g) in H$_2$SO$_4$ (5 ml) was carefully added followed by polyphosphoric acid (40 ml). The reaction mixture was allowed to warm at room temperature and stirred for 3 hrs. Then, the solution was poured into crushed ice and urea was added until gas evolution ceased. The resulting mixture was treated with an aqueos solution of potassium iodide (5.6 g) and heated at 70 for 2 hrs. The reaction mixture was diluited with a 10% solution of sodium hydroxide (40 ml), extracted with ethyl acetate (3×40 ml), washed with brine (3×25 ml), dried and concentrated under vacuum. The title compound was obtained as a red oil (7.5 g).

$^1$H-NMR (CDCl$_3$): 7.67 (1H, d); 7.54 (1H, d).

I.R.(nujol): 1454 cm$^{-1}$, 1350 cm$^{-1}$.

INTERMEDIATE 7

2-Iodo-3,5-Dichloroaniline

To a solution of Intermediate 6 (4 g) in 95% ethanol (35 ml) glacial acetic acid (35 ml) and iron (2.8 g) was added. The reaction mixture was heated at 100° for 1 h then diluited with a satured solution of sodium hydrogencarbonate and extracted with ethyl acetate (3×20 ml). The organic layer was washed with brine (2×20 ml), dried, evaporated under vacuum to give the title compound as brown solid (2.9 g).

IR (nujol): $v_{max}$ (cm$^{-1}$)=3491 (NH2); 3103 (NH2); 1614 (C=C).

INTERMEDIATE 8

(±) 2-(3,5-Dichloro-2-Iodo-Phenylamino)-Pent-4-Enoic Acid Benzyl Ester

To a solution of intermediate 7 (1.5 g) in dry toluene (20 ml) benzylglyoxylate (1.070 g) and $Na_2SO_4$ were added (2.5 g). The mixture was refluxed overnight. After filtration the resulting solution was concentrated under vacuum to a brown oil, which was then taken up with dry dichloromethane (40 ml). After cooling to −78°, $TiCl_4$ (0.57 ml) was slowly added with a syringe and stirring continued for 5 min. The solution was then allowed to warm to room temperature over 30 min by removing the dry ice/acetone bath, then cooled again to −78° and tributylallyltin (1.94 ml) added. After 1 hour the reaction was stopped by pouring it into a saturated solution of $NH_4Cl$ (100 ml). The aqueous phase was extracted with EA (2×200 ml) and the combined organic fractions washed with HCl (3 N, 2×70 ml) and brine (50 ml) and dried. Final purification by column chromatography (CH/EA 95/5) gave the title compound (1.05 g) as a yellow oil.

$^1$ H-NMR ($CDCl_3$): 7.4–7.3 (3H, m); 6.87 (1H, d); 6.27 (1H, d); 5.72 (1H, m); 5.22–5.16 (2H, m); 5.19 (2H, s); 5.14 (1H, d); 4.16 (1H, t); 2.65 (2H, m).

I.R. (neat): 3371 $cm^{-1}$; 1744 $cm^{-1}$; 1572 $cm^{-1}$

INTERMEDIATE 9

(±) 2-(3,5-Dichloro-2-Iodo-Phenylamino)-4-Oxo-Butyric Acid Benzyl Ester

Intermediate 8 (1.0 g) was dissolved in dry dichloromethane (40 ml) and the resulting solution cooled to −78° with a dry ice/acetone bath. Ozone was bubbled through it until a brick-red color appeared (approx 20 min), then triphenylphosphine (0.82 g) was added and the cooling bath removed. After the warm-up was complete the solution was concentrated to dryness and then purified by column chromatography (CH/EA 80/20) to give the title compound (0.745 g) as a colorless oil.

$^1$H-NMR ($CDCl_3$): 9.77 (1H, s); 7.36–7.28 (5H, m); 6.91 (1H, d); 6.40 (1H, d); 5.34 (1H, d); 5.20 (2H, s); 4.50 (1H, dt); 3.09 (2H, d).

I.R. (nujol): 3371 $cm^{-1}$; 1738 $cm^{-1}$, 1732 $cm^{-1}$

INTERMEDIATE 10

(±)(E)2-(3,5-Dichloro-2-Iodo-Phenylamino)-5-Phenylcarbamoyl-Pent-4-Enoic Acid Benzyl Ester Phenylcarbomoylmethyl triphenylphosphonium bromide (0.517 g) was suspended in dry acetonitrile (20 ml) and DBU (0.173 ml) was added with stirring. The reaction mixture was cooled at 0° and intermediate 9 (0.460 g) was added dissolved in dry acetonitrile (8 ml). After 1 h, a satured solution of ammonium chloride (20 ml) was added followed by ethyl acetate (30 ml). The organic layer was separated, washed with brine (2×30 ml), dried and evaporated under vacuum. The crude product was purified by flash chromatography (CH/EA 80/20) to give the title compound (0.250 g) as white solid $^1$H-NMR ($CDCl_3$): 7.54 (2H, 5.06); 7.38–7.3 (7H, m); 7.13 (1H, t); 6.99 (1H, s); 6.90 (1H, d); 6.85 (1H, t); 6.32 (1H, d); 5.26 (1H, d); 4.28 (1H, d); 2.80 (2H, dt). m.p. 146–148°.

INTERMEDIATE 11

(+/−)(E)5,7-Dichloro-4-Phenylcarbamoylmethylene-1,2,3,4-Tetrahydroquinoline-2-Carboxylic Acid Benzyl Ester Intermediate 10 (0.120 g) was dissolved in dry acetonitrile (10 ml) and the solution deoxygenated by bubbling through it dry $N_2$. To this solution, tetrakis (triphenylphosphine)palladium (0.012 g) and triethylamine (0.056 ml) were added and the reaction vessel sealed and heated to 80° for 2 hours. The brown mixture was then cooled, diluted with EA (100 ml) and washed with a saturated solution of $NH_4Cl$ (50 ml). After drying with brine and with $Na_2SO_4$ the crude product was purified by column chromatography (CH/EA 7/3) to give the title compound (0.080 g) as a pale yellow solid.

$^1$H-NMR (DMSO): 9.42 (1H, s); 7.75 (2H, d); 7.35–7.25 (7H, m); 7.07 (1H, tt); 6.78 (1H, s); 6.77 (1H, s); 6.70 (1H, d); 6.44 (1H, m); 5.12 (!h, d); 4.98 (1H, d); 4.40 (1H, ddd); 4.25 (1H, d); 3.15 (1H, d).

I.R. (nujol): 3281 $cm^{-1}$; 1730 $cm^{-1}$; 1661 cm-1, 1626 $cm^{-1}$ m.p. 185–188°.

INTERMEDIATE 12

(+/−)(E)-5-(3,5-Dichloro-2-Iodo-Phenylamino)-Hex-2-Endioic Acid 6-Benzyl Ester

Intermediate 14 (0.2 g) was dissolved in HCOOH (5 ml) and stirred at room temperature for 24 h. The reaction mixture was then evaporated to dryness to give the title compound (0.180 g).

$^1$ H NMR (DMSO): 12.3 (bs, $_1$H); 7.4–7.3 (m, 5H); 7.01 (d, 1H); 6.73 (dt, 1H); 6.66 (d, 1H); 5.87 (d, 1H); 5.37 (d, 1H); 5.18 (s, 2H); 4.73 (dt, 1H); 2.81 (t, 1H).

INTERMEDIATE 13

(+/−)(E)-5-(3,5-Dichloro-2-Iodo-Phenylamino)-1-(4-Acetylamino-Phenylcarbamoyl)-Hex-2-Endioic Acid 6-Benzyl Ester Intermediate 12 (0.18 g) was dissolved in dry THF (5 ml) under nitrogen and triphenylphosphine (0.11 g) and Aldrithiol (0.092 g) were subsequentely added. After 2 hrs at RT, the commercial 4-acetamidoaniline was added at RT and the mixture warmed till reflux. After 2 hrs the solution was reduced to small volume, poured into EA (20 ml) and extracted with water. The crude was evaporated to dryness and columned (CH-EA 20:80) to give 150 mg of the title compound.

$^1$H NMR (DMSO): 9.94 (s, 1H); 9.86 (s, 1H); 7.53 (d, 2H); 7.47 (d, 2H); 7.35–7.3 (m, 5H); 7.24 (dt, 1H); 7.00 (d, 1H); 6.68 (d, 1H); 6.15 (d, 1H); 5.37 (d, 1H); 5.19 (s, 2H); 4.74 (m, 1H); 2.8 (m, 2H); 1.99 (s, 3H). m.p. 200° C.

INTERMEDIATE 14

(+/−)(E)-2-(3,5-Dichloro-2-Iodo-Phenylamino)-Hex-2-Endioic Acid-6-Benzyl-1-Tert-Butylester Intermediate 9 (8.2 g) was dissolved in dry toluene (200 ml), then (tert-butoxycarbonyl methylene) triphenylphosphorane was added and the mixture was stirred at 100° for 2 h. The solvent was removed under vacuum and the crude product was purified by flash-chromatography (CH/EA 95/5) to give the title compound (6.00 g) as a white solid.

$^1$H-NMR ($d_6$-acetone): 7.4–7.3 (m, 5H); 6.92 (d, 1H); 6.82 (dt, 1H); 6.67 (d, 1H), 5.88 (dt, 1H); 5.40 (d, 1H); 5.24 (s, 2H); 4.66 (dt, 1H); 3.0–2.8 (m, 2H); 1.5 (s, 9H) m.p. 95–96° C.

INTERMEDIATE 15

(+/−)(E)-5,7-Dichloro-4-Tert-Butoxycarbonylmethylene-1,2,3,4-Tetrahydroquinoline-2-Carboxylic Acid Benzyl Ester Intermediate 14 (6.5 g) was dissolved in dry dimethylformamide (150 ml). To this solution, tetrakis (triphenylphosphine)palladium (0.65 g) and triethylamine (9.15 ml) were added and the reaction mixture was heated to 100° for 1 h under nitrogen atmosphere. The reaction mixture was then cooled to room temperature, diluted with ethyl acetate (250 ml), washed with a saturated solution of acqueous $NH_4Cl$ (100 ml) and with brine (3×100 ml). The organic layer was separated, dried, filtered and evaporated under vacuum. The crude product was purified by flash chromatography (EA/CH 1/9) to give the title compound (4 g) as a white solid.

$^1$H -NMR(DMSO): 7.44–7.3 (m, 5H); 6.77 (d, $_1$H); 6.70 (d, 1H); 6.47 (bs, 1H); 6.45 (s, 1H); 5.21 (d, 1H); 5.02 (d, 1H); 4.40 (td, 1H); 3.98 (dd, 1H); 3.11 (ddd, 1H); 1.5 (s, 9H).

INTERMEDIATE 16

(+/−)(E)-5,7-Dichloro-4-Carboxymethylene-1,2,3,4-Tetrahydro-Quinoline-2-Carboxylic Acid Benzyl Ester Intermediate 15 (0.96 g) was suspended in formic acid (40 ml) and stirred at room temperature for 2 hours. The solvent was removed under vacuum, then the solid was suspended in ether and then concentrated again to dryness to give the title compound (0.86 mg) as a white solid.

$^1$H-NMR ($d_6$-acetone): 11.2–10.6 (bs, 1H); 7.4–7.3 (m, 5H); 6.78 (d, 1H); 6.71 (d, 1H); 6.57 (s, 1H); 6.49 (bs, 1H); 5.18 (d, 1H), 5.03 (d, 1H); 4.41 (t, 1H); 4.05–4 (m, 1H); 3.14 (ddd, 1H)

I.R.(Nujol): 3373 $cm^{-1}$; 1726 $cm^{-1}$; 1688 $cm^{-1}$; 1614 $cm^{-1}$ m.p. 210–212° C.

INTERMEDIATE 17

(+/−)(E)-5,7-Dichloro-4-[2-(Pyridyl) Thiocarbonylmethylene]-1,2,3,4-Tetrahydro-Quinoline-2-Carboxylic Acid Benzyl Ester Intermediate 16 (3.7 g) was dissolved in dry tetrahydrofuran (50 ml). To this solution, triphenylphosphine (6.17 g) and 2,2'-dithiopyridine (5.2 g) were added and the reaction mixture was stirred for 1 h at room temperature under nitrogen atmosphere. The reaction mixture was diluted with ethyl acetate (200 ml), then washed with HCl 1 N (50 ml), NaOH 2 M (50 ml) and brine (2×50 ml). The organic layer was separated, dried, filtered and evaporated under vacuum. The crude product was purified by flash chromatography (EA/CH 3/7) to give the title compound (3.5 g) as a yellow foam.

$^1$H -NMR(DMSO): 8.59 (m, 1H); 7.78 (dt, 1H); 7.62 (m, 2H); 7.45–7.27 (m, 5H); 6.84–6.76 (s, 3H); 5.15 (d, 1H); 4.97 (d, 1H); 4.40 (m, 1H); 3.92 (dd, 1H); 2.80 (m, 1H).

INTERMEDIATE 18

(+/−)(E)4-(4-Acetylamino-Phenylcarbamoylmethylene)-5,7-Dichloro-1,2,3,4-Tetrahydro-Quinoline-2-Carboxylic Acid Benzyl Ester Intermediate 13 (0.14 g) was dissolved in dry acetonitril (11 ml) under nitrogen and Pd tetrakistriphenylphosphine (0.012 g) and TEA (0.06 ml) were subsequentely added. The suspension was stirred and warmed to reflux till completion of the reaction. After cooling a white solid precipitated to give the title compound (30 mg) after filtration.

$^1$H NMR (DMSO): 10.12 (s, 1H), 9.86 (s, 1H); 7.56 (d, 2H); 7.47 (d, 2H); 7.3–7.2 (m, 5H); 6.71 (d, 1H); 6.69 (d, 1H); 6.68 (bm, 1H); 5.05 (d, 1H); 4.85 (d, 1H); 4.35 (m, 1H); 4.25 (dd, 1H); 2.0 (s, 3H). m.p. 275° C.

INTERMEDIATE 19

(+/−)(E)-4-(3-Acetylamino-Phenylcarbamoylmethylene)-5,7-Dichloro-1,2,3,4-Tetrahydro-Quinoline-2-Carboxylic Acid Benzyl Ester Intermediate 16 (0.080 g) was dissolved in dry tetrahydrofuran (7 ml) and the solution was cooled to −20°. At the same temperature $PCl_5$ (0.053 g) was added and the reaction mixture was warmed to 0° C. and stirred for 1 h under nitrogen atmosphere. Pyridine (0.025 ml) and 3-acetylaminoaniline (0.035 g) were then added and the reaction mixture was stirred for 3 h at room temperature. The reaction mixture was then diluted with ethyl acetate (50 ml), washed with HCl 1 N (50 ml), and with brine (50 ml). The organic layer was separated, dried, filtered and evaporated under vacuum to give a crude product which was purified by flash chromatography (EA/CH 6:4) to give the title compound (0.045 g) as a yellow oil.

$^1$H NMR (DMSO): 10.19 (s, 1H); 9.93 (s, 1H); 7.99 (s, 1H); 7.24 (m, 5H); 7.38–7.16 (m, 4H); 6.73 (bs, 1H); 6.72 (d, 1H); 6.70 (d, 1H); 5.07–4.8 (d, 2H); 4.35 (m, 1H); 4.22 (m, 1H); 2.02 (s, 3H).

IR (nujol): 3304, 1732, 1668, 1600.

INTERMEDIATE 20

(+/−)(E)-5,7-Dichloro-4-[3-(Chloro) Phenylcarbamoylmethylene]-1,2,3,4-Tetrahydro-Quinoline-2-Carboxylic Acid Benzyl Ester Intermediate 16 (0.11 g) was dissolved in THF (10 ml), the resulting solution was cooled at −20° and $PCl_5$ (0.10 g) was added. The mixture was stirred for 1 hour at 0°, then the temperature was lowered to −20° and pyridine (0.045 ml) and 3-chloro aniline (0.037 ml) were added. The reaction was stirred at room temperature for 14 hours then diluted with EA (100 ml) and washed with a saturated solution of $NH_4Cl$ (2×50 ml), with HCl 0.1 N (50 ml) and brine (50 ml). The organic layer was dried, and evaporated under vacuum. The crude product was purified by flash-chromatography (CH/EA 9/1 to 8/2) to give the title compound (0.05 g) as a yellow solid.

$^1$H-NMR (DMSO): 10.36 (bs, 1H); 7.94 (bs, 1H); 7.43 (d, 1H); 7.33 (d, 1H); 7.28 (bd, 1H); 7.10 (dt, 1H); 7.24 (m, 5H); 6.72 (m, 3H); 5.03 (d, 1H); 4.85 (d, 1H); 4.38 (m, 1H); 4.26 (dd, 1H); 2.78 (dd, 1H)

I.R.(Nujol): 3340 $cm^{-1}$; 1732 $cm^{-1}$; 1659 $cm^{-1}$

INTERMEDIATE 21

(+/−)(E)-4-(4-Amino-Phenylcarbamoylmethylene)-5,7-Dichloro-1,2,3,4-Tetrahydro-Quinoline-2-Carboxylic Acid Benzyl Ester Intermediate 23 (0.175 g) was suspended in dry dichloromethane (5 ml) and TFA (0.10 ml) was added at RT and the solution stirred for 4 h. The solution was evaporated to dryness to give a crude solid which was dissolved in EA and washed with saturated sodium carbonate solution. The organic phase was evaporated to dryness to give a crude which was triturated with pentane giving the title compound (0.116 g).

$^1$H NMR (DMSO): 9.79 (s, 1H); 7.31 (d, 2H); 7.3–7.2 (m, 5H); 7.19 (d, 1H) 6.70 (d, 1H); 6.69 (d, 1H); 6.64 (m, 1H);

6.48 (d, 2H); 5.05 (d, 1H); 4.85 (d, 1H); 4.33 (m, 1H); 4.24 (dd, 1H); 2.80 (s, 1H). m.p. 80° C.

INTERMEDIATE 22

4,6-Dibromo-1-Iodo-2-Nitrobenzene 2-nitro-4,6-dibromoaniline (2 g) was dissolved in a 12 N solution of $H_2SO_4$ (14 ml) and cooled at 0°. Then, a solution of $NaNO_2$ (0.6 g) in $H_2SO_4$ (5 ml) was carefully added followed by PPA (10 ml). The reaction mixture was allowed to warm at room temperature and stirred for 3 hrs. Then, the solution was poured into crushed ice and urea was added until gas evolution ceases.

The resulting mixture was treated with an aqueos solution of potassium iodide (1.6 g) and heated at 70° for 2 hrs. The reaction mixture was diluited with a 10% solution of sodium hydroxide (20 ml), extracted with ethyl acetate (3×20 ml), washed with brine (3×15 ml), dried and concentrated under vacuum. The title compound was obtained as a yellow solid (2.6 g).

$^1$H-NMR (CDCl$_3$): 7.98 (1H, d); 7.60 (1H, d);

I.R.(nujol): 1529 cm$^{-1}$, 1377 cm$^{-1}$. m.p. (°C.): 68° C.–70° C.

INTERMEDIATE 23

(+/−)(E)-4-(4-Tert-Butoxycarbonylamino-Phenylcarbamoylmethylene)-5,7-Dichloro-1,2,3,4-Tetrahydro-Quinoline-2-Carboxylic Acid Benzyl Ester Intermediate 16 (0.157 g) was dissolved in dry THF (8 ml) and the solution cooled to −20°. PCl$_5$ (0.104 g) was added and the solution stirred for 1 h. Pyridine (0.05 ml) was added and then 4-t-Butoxycarbonylaminoaniline (0.104 g) was added in one portion. The solution became orange and was warmed to RT. After 3 hrs the solution was acidified to pH=3, extracted with EA and evaporated to dryness to give a crude solid which was triturated with pentane/diethyl ether to give the title compound (0.181 g).

$^1$H NMR (DMSO): 9.35 (bs, 1H); 8.23 (bs, 1H); 7.66 (m, 2H); 7.48 (m, 2H); 7.35–7.28 (m, 5H); 6.76 (m, 2H); 6.68 (d, 1H); 6.42 (bs, 1H); 5.13 (d, 1H); 4.97 (d, 1H); 4.39 (t, 1H); 4.23 (dd, 1H); 3.18 (dd, 1H); 1.48 (s, 9H).

INTERMEDIATE 24

(+/−)(E)-5,7-Dichloro-4-[4(Tert-Butoxycarbonylaminomethyl)Phenylcarbamoyl Methylene]-1,2,3,4-Tetrahydro-Quinoline-2-Carboxylic Acid Benzyl Ester Intermediate 16 (0.57 g) was dissolved in THF (15 ml), the resulting solution was cooled at −20° and PCl$_5$ (0.38 g) was added. The mixture was stirred for 1 hour at 0°, then the temperature was lowered to −20° and pyridine (0.176 ml) and N-t-butoxycarbonyl-4-amino benzylamine (0.39 g) were added. The reaction was stirred at room temperature for 30 min then diluted with EA (100 ml) and washed with a saturated solution of NH$_4$Cl (2×50 ml), with HCl 0.1 N (50 ml) and brine (50 ml). The organic layer was dried and evaporated under vacuum. The crude product was purified by flash-chromatography (CH/EA 8/2 to 7/3) to give the title compound (0.72 g) as a white solid.

$^1$H-NMR (d$_6$-acetone): 9.42 (bs, 1H); 7.69 (d, 2H); 7.33 (dd, 2H); 7.3–7.27 (m, 3H); 7.26 (d, 2H); 6.78 (d, 1H); 6.77 (s, 1H); 6.69 (d, 1H); 6.44 (d, 1H); 6.42 (t, 1H); 5.12 (d, 1H); 4.97 (d, 1H); 4.40 (td, 1H); 4.25 (dd, 1H); 4.23 (d, 1H); 3.13 (ddd, 1H); 1.42 (s, 9H)

I.R.(Nujol): 3368 cm$^{-1}$; 3304 cm$^{-1}$; 1717 cm$^{-1}$

INTERMEDIATE 25

(+/−)(E)-5,7-Dichloro-4-[4-(2-Tert-Butoxycarbonylamino-Ethyl)Phenylcarbamoylmethylene]-1,2,3,4-Tetrahydro-Quinoline-2-Carboxylic Acid Benzyl Ester Intermediate 17 (0.3 g) was dissolved in dry tetrahydrofuran (20 ml) and toluene (20 ml). To this solution, 4-(2-tert-butylamino-ethyl)aniline (0.175 g) was added and the reaction mixture was stirred for 2 h at 110°. The reaction mixture was then diluted with ethyl acetate (50 ml), washed with a HCl 0.1 N (50 ml), and with brine (50 ml). The organic layer was separated, dried, filtered and evaporated under vacuum to give a crude product which was purified by flash chromatography (EA/CH 3:7) to give the title compound (0.360 g) as a yellow solid.

$^1$H NMR (DMSO): 10.12 (s, 1H); 7.55 (d, 2H); 7.24 (m, 5H); 7.10 (d, 2H); 6.85 (t, 1H); 6.70 (m, 3H); 5.04–4.84 (d, d, 2H); 4.35 (m, 1H); 4.25 (m, 1H); 3.10 (m, 2H); 2.79 (m, 1H); 2.62 (t, 2H); 1.34 (s, 9H).

IR (nujol): 3368, 3298, 1700, 1686.

INTERMEDIATE 26

(+/−)(E)-5,7-Dichloro-4-[4(Ureidomethyl)Phenylcarbamoylmethylene]-1,2,3,4-Tetrahydro-Quinoline-2-Carboxylic Acid Benzyl Ester Intermediate 24 (0.36 g) was suspended in dry dichloromethane (20 ml), then trifluoroacetic acid (7.5 ml) was added and the reaction was stirred at room temperature for 1 hour. The solvent was removed under vacuum to give a solid which was suspended in ether and evaporated to dryness. This solid was dissolved in dry THF (50 ml), then dry TEA (0.14 ml) was added and the mixture stirred at room temperature for 1.5 hours. The reaction was then cooled to 0° and trimethylsilyl isocyanate (0.164 ml) was dropped in. After 1 hour the reaction was stopped by pouring it into a saturated solution of NH$_4$Cl (50 ml). The aqueous phase was extracted with EA (100 ml), washed with brine (50 ml) and evaporated under vacuum. The crude product was purified by flash-chromatography (EA to EA/MeOH 95/5) to give the title compound (0.14 g) as a yellow solid.

$^1$H-NMR (DMSO): 10.15 (s, 1H); 7.58 (d, 2H); 7.25 (bm, 5H); 7.24 (m, 1H); 7.17 (d, 2H); 6.71 (m, 3H); 6.33 (bt, 3H); 5.48 (bs, 2H); 5.06 (d, 1H); 4.85 (d, 1H); 4.36 (mt, 1H); 4.25 (dd, 1H); 4.11 (m, 2H); 2.81 (ddd, 1H)

INTERMEDIATE 27

(+/−)(E)5,7-Dichloro-4-[4(Formylaminomethyl)Phenylcarbomoylmethylene]-1,2,3,4-Tetrahydro-Quinoline-2-Carboxylic Acid Benzyl Ester Intermediate 24 (0.18 g) was dissolved in formic acid (10 ml) and stirred at room temperature for 15 min. The solvent was removed under vacuum to give a solid which was suspended in ether and evaporated to dryness. This solid was dissolved in dry THF (10 ml), then dry TEA (0.09 ml) was added and the mixture stirred at room temperature for 30 min. The reaction was then cooled to 0° and methanesulphonylchloride (0.025 ml) was dropped in. After 30 min the reaction was stopped by pouring it into a saturated solution of NH$_4$Cl (50 ml). The aqueous phase was extracted with EA (100 ml), washed with brine (50 ml), dried and evaporated under vacuum. The crude product was purified by flash-chromatography (CH/EA 1/1) to give the title compound (0.050 g) as a byproduct.

$^1$H-NMR (DMSO): 10.2 (bs, 1H); 8.44 (t, 1H); 8.10 (d, 1H); 7.60 (d, 2H); 7.26–7.20 (m, 6H); 7.18 (d, 2H); 6.72–6.68 (m, 3H), 5.04 (d, 1H); 5.40 (d, 1H); 4.35 (m, 1H); 4.25 (m, 1H); 4.23 (d, 2H); 2.80 (dd, 1H)

INTERMEDIATE 28

(+/−)(E)-5,7-Dichloro-4-[4(Acetylaminomethyl) Phenylcarbomoylmethylene]-1,2,3,4-Tetrahydro-Quinoline-2-Carboxylic Acid Benzyl Ester Intermediate 24 (0.08 g) was dissolved in dry dichloromethane (10 ml), then trifluoroacetic acid (1 ml) was added and the reaction was stirred at room temperature for 2 hour. The solvent was removed under vacuum to give a solid which was suspended in ether and evaporated to dryness. This solid was dissolved in dry THF (15 ml), then dry TEA (0.04 ml) was added and the mixture stirred at room temperature for 1 hours. The reaction was then cooled to 0° and acetylchloride (0.01 ml) was dropped in. After 40 min the reaction was stopped by pouring it into a saturated solution of NH$_4$Cl (50 ml). The aqueous phase was extracted with EA (100 ml), washed with brine (50 ml), dried and evaporated under vacuum. The crude product was purified by flash-chromatography (EA/CH 9/1) then the solid was suspended in EA, petroleum ether was added and the solid was filtered to give the title compound (0.045 g) as a yellow solid.

$^1$H-NMR (d$_6$-acetone): 9.41 (bs, 1H); 7.68 (d, 2H); 7.5–7.25 and 7.24 (m, 6H); 6.77 (d, 1H); 6.76 (bs, 1H); 6.69 (d, 1H); 6.44 (bs, 1H); 5.12 and 4.96 (d, 2H); 4.39 (m, 1H); 4.32b (d, 2H); 4.25 (dd, 1H); 3.14 (ddd, 1H)

INTERMEDIATE 29

(+/−)(E)-5,7-Dichloro-4-[4(Isobutyrylamino) Phenylcarbomoylmethylene]-1,2,3,4-Tetrahydro-Quinoline-2-Carboxylic Acid Benzyl Ester Intermediate 23 (0.15 g) was dissolved in dry dichloromethane (20 ml), then trifluoroacetic acid (2 ml) was added and the reaction was stirred at room temperature for 2 hour. The solvent was removed under vacuum to give a solid which was suspended in ether and evaporated to dryness. This solid was dissolved in dry THF (20 ml), then dry TEA (0.08 ml) was added and the mixture stirred at room temperature for 1 hour. The reaction was then cooled to 0° and isobutyrylchloride (0.03 ml) was dropped in. After 40 min the reaction was stopped by pouring it into a saturated solution of NH$_4$Cl (50 ml). The aqueous phase was extracted with EA (100 ml), washed with brine (50 ml), dried and evaporated under vacuum. The crude product was purified by flash-chromatography (EA/CH 2/3) to give the title compound (0.040 g) as a yellow solid.

$^1$H-NMR (DMSO): 10.11 (bs, 1H); 9.74 (bs, 1H); 7.56 (d, 2H); 7.52 (d, 2H); 7.26 (m, 5H); 7.22 (d, 1H); 6.70 (m, 3H); 5.04 (d, 1H); 4.86 (d, 1H); 4.36 (m, 1H); 4.25 (m, 1H); 2.83 (m, 1H); 2.51 (m, 1H); 1.07 (d, 6H)

I.R.(Nujol): 3387 cm$^{-1}$; 3292 cm$^{-1}$; 1715 cm$^{-1}$; 1661 cm$^{-1}$; 1658 cm$^{-1}$

INTERMEDIATE 30

(+/−)(E)-5,7-Dichloro-4-[4(Isobutyrylaminomethyl) Phenylcarbamoylmethylene]-1,2,3,4-Tetrahydro-Quinoline-2-Carboxylic Acid Benzyl Ester Intermediate 24 (0.36 g) was suspended in dry dichloromethane (20 ml), then trifluoroacetic acid (7.5 ml) was added and the reaction was stirred at room temperature for 1 hour. The solvent was removed under vacuum to give a solid which was suspended in ether and evaporated to dryness. This solid was dissolved in dry THF (50 ml), then dry TEA (0.23 ml) was added and the mixture stirred at room temperature for 1.5 hours. The reaction was then cooled to 0° and isobutyrylchloride (0.09 ml) was dropped in. After 1 hour the reaction was stopped by pouring it into a saturated solution of NH$_4$Cl (50 ml). The aqueous phase was extracted with EA (100 ml), washed with brine (50 ml) and evaporated under vacuum. The crude product was purified by flash-chromatography (CH/EA 6/4 to 1/1) and triturated with petroleum ether to give the title compound (0.14 g) as a yellow solid.

$^1$H-NMR (d$_6$-acetone): 9.42 (bs, 1H); 7.68 (d, 2H); 7.35 (bm, 1H); 7.34 (dd, 2H); 7.28 (m, 3H); 7.23 (d, 2H); 6.77 (d, 1H); 6.76 (bs, 1H); 6.69 (d, 1H); 6.44 (d, 1H); 5.12 (d, 1H); 4.96 (d, 1H); 4.40 (td, 1H); 4.34 (d, 2H); 4.25 (dd, 1H); 4.23 (d, 1H); 3.13 (ddd, 1H); 1.42 (s, 9H)

I.R.(Nujol): 3368–3290 cm$^{-1}$; 1724 cm$^{-1}$; 1647 cm$^{-1}$; 1591 cm$^{-1}$

INTERMEDIATE 31

(+/−)(E)-5,7-Dichloro-4-(4-Morpholin-4-Ylmethylphenylcarbamoylmethylene)-1,2,3,4-Tetrahydro-Quinoline-2-Carboxylic Acid, Benzyl Ester To a stirred solution of intermediate 17 (0.15 g) in dry tetrahydrofuran (10 ml) was added 4-morpholin-4-ylmethyl-phenylamine (0.09 g) and the reaction mixture was heated at reflux for 4 hrs. The solvent was evaporated, the residue was dissolved in toluene (10 ml) and the solution was heated at reflux for 1 hrs. The reaction mixture was cooled at 24°, affording a precipitate which was filtered to obtain the pure title compound (0.11 g). T.l.c. ethyl acetate, R$_f$=0.42.

1H-NMR(DMSO): 10.17 (s, 1H), 7.60 (d, 2H), 7.21 (m, 8H), 6.72–6.70 (m, 3H), 5.03 (d, 1H), 4.83 (d, 1H), 4.36 (m, 1H), 4.25 (dd, 1H)., 3.54 (t, 4H), 3.38 (s, 2H), 2.8 (dd, 1H), 2.30 (m, 4H).

INTERMEDIATE 32

(+/−)(E)-4-(4-Methoxycarbonylmethyl-Phenylcarbamoylmethylene)-5,7-Dichloro-1,2,3,4-Tetrahydro-Quinoline-2-Carboxylic Acid Benzyl Ester Intermediate 17 (0.121 g) was dissolved in dry toluene (10 ml). To this solution, methyl 4-(aminophenyl)acetate (0.052 g) was added and the reaction mixture was refluxed for 1 h. The reaction mixture was then cooled and a precipitate was formed which was filtered and washed with diethyl ether to give the title compound (0.099 g) as a yellow solid.

$^1$H NMR (DMSO): 10.2 (s, 1H); 7.59 (d, 2H); 7.26–7.2 (m, 6H); 7.18 (d, 2H); 6.72–6.70 (m, 3H); 5.04 (d, 1H); 4.84 (d, 1H); 4.36 (m, 1H); 4.25 (dd, 1H); 3.61 (s, 2H); 3.59 (s, 3H); 2.79 (dd, 1H).

IR (nujol): 3358, 3308, 1722, 1649.

INTERMEDIATE 33

(+/−)(E)-5,7-Dichloro-4-(4-Carbamoylmethyl-Phenylcarbamoylmethylene)-1,2,3,4-Tetrahydro-Quinoline-2-Carboxylic Acid Benzyl Ester Intermediate 17 (0.2 g) was dissolved in dry dimethylformamide (30 ml). To this solution, 4-carbamoylmethylaniline (0.073 g) was added and the reaction mixture was stirred for 2 h at 100°. The reaction mixture was then diluted with ethyl acetate (50 ml), washed with a saturated acqueous solution of $NH_4Cl$ (50 ml), and with brine (50 ml). The organic layer was separated, dried, filtered and evaporated under vacuum to give a crude product which was triturated in ethyl acetate (5 ml) and petroleum ether (20 ml) to give the title compound (0.150 g) as a yellow solid.

$^1$H NMR (DMSO): 10.2 (bs, 1H); 7.56 (d, 2H); 7.40 (bs, 1H); 7.26–7.20 (m, 6H); 7.17 (d, 2H); 6.84 (bs, 1H); 6.72–6.70 (m, 3H); 5.04 (d, 1H); 4.84 (d, 1H); 4.35 (m, 1H); 4.25 (dd, 1H); 2.79 (dd, 1H);

IR (nujol): 3366, 3287, 1715, 1653.

INTERMEDIATE 34

(+/−)(E)-5,7-Dichloro-4-[4-(2-Isobutirylamino-Ethyl)Phenylcarbamoylmethylene]-1,2,3,4-Tetrahydro-Quinoline-2-Carboxylic Acid Benzyl Ester Intermediate 17 (0.2 g) was dissolved in dry tetrahydrofurane (15 ml) and dry toluene (15 ml). To this solution, 4-(2-tert-butoxycarbonylaminoethyl)aniline (0.127 g) was added and the reaction mixture was heated for 2 h at 110°. The reaction mixture was then diluted with ethyl acetate (50 ml), washed with HCl 0.1 N (50 ml) and with brine (50 ml). The organic layer was separated, dried, filtered and evaporated under vacuum to give a yellow oil (0.4 g) that was dissolved in dry dichloromethane (10 ml). To this solution, trifluoroacetic acid (1 ml) was added and the reaction mixture was stirred for 2 h at room temperature under nitrogen atmosphere and then evaporated under vacuum to give a dark yellow oil that was dissolved in dry tetrahydrofuran (10 ml). Triethylamine (0.073 ml) was then added and the solution was stirred for 1 h at room temperature; isobutiryl chloride (0.052 ml) was then added and the resulting reaction mixture was stirred for 2 h at room temperature. The reaction mixture was then diluted with ethyl acetate (50 ml), washed with a saturated acqueous solution of $NH_4Cl$ (50 ml) and with brine (50 ml). The organic layer was separated, dried, filtered and evaporated under vacuum to give the title compound (0.120 g) as a yellow solid.

$^1$H NMR (DMSO): 10.12 (s, 1H); 7.74 (t, 1H); 7.56 (d, 2H); 7.24 (m, 5H); 7.11 (d+s, 3H); 6.70 (m, 3H); 5.05 (d, 1H); 4.85 (d, 1H); 4.36 (m, 1H); 4.25 (dd, 1H); 3.21 (m, 2H); 2.80 (dd, 1H); 2.63 (m, 2H); 2.28 (m, 1H); 0.94 (d, 6H). m.p. 180–182° C.

INTERMEDIATE 35

(+/−)(E)-5,7-Dichloro-4-[4-(2-Acetylamino-Ethyl)Phenylcarbamoylmethylene]-1,2,3,4-Tetrahydro-Quinoline-2-Carboxylic Acid Benzyl Ester Intermediate 25 (0.180 g), was dissolved in dry dichloromethane (10 ml). To this solution, trifluoroacetic acid (2 ml) was added and the reaction mixture was stirred for 2 h at room temperature under nitrogen atmosphere and then evaporated under vacuum to give a dark yellow oil that was dissolved in dry tetrahydrofuran (10 ml). Triethylamine (0.088 ml) was then added and the solution was stirred for 1 h at room temperature; acetyl chloride (0.025 ml) was then added and the resulting reaction mixture was stirred for 3 h at room temperature. The reaction mixture was then diluted with ethyl acetate (50 ml), washed with a saturated acqueous solution of $NH_4Cl$ (50 ml) and with brine (50 ml). The organic layer was separated, dried, filtered and evaporated under vacuum to give the title compound (0.110 g) as a white solid.

$^1$H NMR (DMSO): 10.129 (s, 1H); 7.88 (t, 1H); 7.56 (d, 2H); 7.24 (m, 5H); 6.71 (d, 1H) 6.70 (d, 1H); 6.70 (bs, 1H); 6.12 (d, 2H); 5.05 (d, 1H); 4.85 (d, 1H); 4.35 (m, 1H); 4.24 (m, 1H), 3.21 (m, 2H); 2.83 (m, 1H); 2.63 (m, 2H); 1.76 (s, 3H). m.p. 235–238° C.

IR (nujol): 3288, 1747, 1724, 1624–1600.

INTERMEDIATE 36

N-(4-T-Butoxycarbonylamino-Phenyl)-3-Methyl-Butyramide

To a stirred solution of N-t-butoxycarbonyl-1,4-phenylene diamine (0.2 g) in dry tetrahydrofuran (20 ml) were added pyridine (0.15 ml) and 3-methylbutyryl chloride (0.13 g) and the reaction mixture was stirred for 1 hrs. The solution was diluted with ethyl acetate (50 ml), washed with a 3 N solution of hydrochloric acid (30 ml) and brine (30 ml), dried and concentrated in vacuum to give the title compound (0.27 g). T.l.c. cyclohexane/ethyl acetate 1/1, $R_f$=0.71.

1H-NMR(CDCl$_3$): 7.43 (d, 2H), 7.30 (d, 2H), 7.05 (bs, 1H), 6.43 (bs, 1H), 2.25–2.18 (m, 3H), 1.51 (s, 9H), 1.01 (d, 6H).

INTERMEDIATE 37

N-(4-Aminophenyl)-3-Methyl-Butyramide

A solution of intermediate 36 (0.27 g) in dichloromethane/trifluoroacetic acid (5 ml/5 ml) was stirred for 45 min. The solvent was evaporated, the crude product was diluted with ethyl acetate (50 ml), washed with a 5% solution of sodium hydroxyde (30 ml) and brine (30 ml), dried and concentrated in vacuum. The crude product was purified by silica gel column chromatography using ethyl acetate as eluant to give the title compound (0.177 g). T.l.c. ethyl acetate, R=0.52.

1H-NMR(DMSO): 9.37 (s, 1H), 7.18 (d, 2H), 6.45 (d, 2H), 4.80 (s, 2H), 2.1–1.95 (m, 3H), 0.89 (d, 6H).

INTERMEDIATE 38

(+/−)(E)-5,7-Dichloro-4-[4-(3-Methyl-Butyrylamino)-Phenylcarbamoylmethylene]-1,2,3,4-Tetrahydro-Quinoline-2-Carboxylic Acid, Benzyl Ester To a stirred solution of intermediate 17 (0.05 g) in dry toluene (6 ml) was added intermediate 37 (0.043 g) and the reaction mixture was heated at reflux for 1 hrs. The reaction mixture was cooled at 24°, affording a precipitate which was filtered to obtain the pure title compound (0.05 g). T.l.c. EA/CH 1/1, $R_f$=0.62.

1H-NMR(DMSO): 10.12 (s, 1H), 9.78 (s, 1H), 7.56 (d, 2H), 7.50 (d, 2H), 7.25 (m, 6H), 6.71 (d, 1H), 6.69 (d, 1H), 6.69 (s, 1H) 5.06 (d, 1H), 4.85 (d, 1H), 4.33 (m, 1H), 4.25 (dd, 1H), 2.82 (dd, 1H), 2.14 (d, 2H), 2.05 (m, 1H), 0.91 (d, 6H).

INTERMEDIATE 39

2-Iodo-3,5-Dibromoaniline

Intermediate 22 (1.5 g) was dissoved in 95% ethanol (12 ml) and glacial acetic acid (12 ml) and iron (0.823 g) was added. The reaction mixture was heated at 100° for 1 h then diluited with a satured solution of sodium hydrogencarbonate and extracted with ethyl acetate (3×10 ml). The organic layer was washed with brine (2×10 ml), dried, evaporated under vacuum to give the title compound as brown oil (1.15 g).

$^1$H-NMR (CDCl$_3$): 7.20 (1H, d); 6.80 (1H, d); 4.40 (2H, bs).

I.R.(nujol): 1609 cm$^{-1}$, 1580 cm$^{-1}$, 1592 cm$^{-1}$

INTERMEDIATE 40

(+/−)2-(3,5-Dibromo-2-Iodo-Phenylamino)Pent-4-Enoic Acid Benzyl Ester

To a solution of 2-iodo-3,5-dibromoaniline (1.1 g) in dry toluene (20 ml) were added benzylglyoxylate (0.530 g) and Na$_2$SO$_4$ (1 g). The mixture was refluxed overnight. After filtration the resulting solution was concentrated under vacuum to a brown oil, which was then taken up with dry dichloromethane (20 ml). After cooling to −78°, TiCl$_4$ (0.318 ml) was slowly added with a syringe and stirring continued for 5 min. The solution was then allowed to warm to room temperature over 30 min by removing the dry ice/acetone bath, then cooled again to −78° and tributylallyltin (0.98 ml) added. After 1 hour the reaction was stopped by pouring it into a saturated solution of NH$_4$Cl (80 ml). The aqueous phase was extracted with EA (2×100 ml) and the combined organic fractions washed with HCl (3 N, 2×30 ml) and brine (50 ml) and dried. Final purification by column chromatography (CH/EA 8/2) gave the title compound (0.6 g) as a yellow oil.

$^1$H-NMR (CDCl$_3$): 7.4 −7.3 (3H, m); 6.87 (1H, d); 6.27 (1H, d); 5.72 (1H, m); 5.22–5.16 (2H, m); 5.19 (2H, s); 5.14 (1H, d); 4.16 (1H, t); 2.65 (2H, m).

I.R. (neat): 3371 cm$^{-1}$; 1744 cm$^{-1}$; 1572 cm$^{-1}$

INTERMEDIATE 41

(+/−)2-(3,5-Dibromo-2-Iodo-Phenylamino)-4-Oxo-Butyric Acid Benzyl Ester

Intermediate 40 (0.45 g) was dissolved in dry dichloromethane (20 ml) and the resulting solution cooled to −78° with a dry ice/acetone bath. Ozone was bubbled through it until a brick-red color appeared (approx 20 min), then triphenylphosphine (0.4 g) was added and the cooling bath removed. After the warm-up was complete the solution was concentrated to dryness on the rotary evaporator and finally purified by column chromatography (CH/EA 80/20) to give the title compound (0.22 g) as a colorless oil.

$^1$H-NMR (DMSO): 9.64 (1H, t); 7.26–7.36 (5H, m); 7.21 (1H, d); 6.87 (1H, d); 5.63 (1H, d); 5.13 (2H, s); 4.91 (1H, dt); 3.17 (1H, ddd); 3.09 (1H, ddd).

I.R. (nujol): 3371 cm$^{-1}$; 1738 cm$^{-1}$, 1732 cm$^{-1}$

INTERMEDIATE 42

(+/−)-(E)-2-(3,5-Dibromo-2-Iodo-Phenylamino)-5-Phenylcarbamoyl-Pent-4-Enoic Acid Benzyl Ester Phenylcarbamoilmethylene triphenylphosphonium bromide (0.2 g) was suspended in dry acetonitrile (15 ml) and DBU (0.066 ml) was added with stirring. The reaction mixture was cooled at 0° and intermediate 41 (0.210 g) was added dissolved in dry acetonitrile (8 ml). After 1 h, a satured solution of ammonium chloride (10 ml) was added followed by ethyl acetate (30 ml). The organic layer was separated, washed with brine (2×10 ml), dried and evaporated under vacuum. The crude product was purified by flash cromatography (CH/EA 70/30) to give the title compound (0.150 g) as white solid (pure E isomer).

$^1$H-NMR (CDCl$_3$): 7.54 (2H, bd); 7.4–7.3 (7H, m); 7.13 (1H, t); 7.00 (1H, s); 6.90 (1H, s); 6.85 (1H, dt); 6.49 (1H, d); 5.26 (1H, d); 4.28 (1H, d); 2.77–2.83 (2H, m). m.p. (°C.): 168–170° C.

INTERMEDIATE 43

(+/−)-(E)-5,7-Dibromo-4-Phenylcarbamoylmethylene-1,2,3,4-Tetrahydroquinoline-2-Carboxylic Acid Benzyl Ester Intermediate 42 (0.130 g) was dissolved in dry acetonitrile (10 ml) and the solution deoxygenated by bubbling through it dry N$_2$. To this solution, Pd(PPh$_3$)$_4$ (0.011 g) and triethylamine (0.053 ml) were added and the reaction vessel sealed and heated to 80° for 4 hours. The brown mixture was then cooled, diluted with EA (100 ml) and washed with a saturated solution of NH$_4$Cl (50 ml). After drying with brine and with Na$_2$SO$_4$ the crude product was purified by column chromatography (CH/EA 75/25) to give the title compound (0.048 g) as a pale yellow solid.

$^1$H-NMR (DMSO): 9.45 (1H, s); 7.77 (2H, m); 7.35–7.28 (7H, m); 7.07 (1H, m); 7.02 (1H, d); 6.96 (1H, d); 5.12 (1H, d); 4.96 (1H, d); 4.40 (1H, m); 4.22 (1H, dd); 3.17 (1H, ddd). m.p. (°C.) 184–186° C.

EXAMPLE 1

(+/−)(E)7-Chloro-4-Phenylcarbamoylmethylene-1,2,3,4-Tetrahydro-Quinoline-2-Carboxylic Acid To the stirred solution of Intermediate 5 (0.035 g) in 4/1 EtOH/H$_2$O (2 ml) LiOH*H2O (0.007 g) was added. Stirring was continued at room temperature for 1.5 hours. After concentrating the solution to approximately 0.5 ml, HCl (3 N, 5 ml) was added and the precipitate thus formed filtered, washed with small amounts of cold water and dried under vacuum to give the title compound (0.022 g) as a yellow solid.

$^1$H NMR: d (CDCl$_3$) 12.71 (bs, 1H), 10.01 (bs, 1H), 7.62 (m, 2H), 7.38 (d, 1H), 7.29 (m, 2H), 7.01 (m, 1H), 6.80 (bd, 1H), 6.78 (d, 1H), 6.59 (dd, 1H), 6.49 (s, 1H), 4.03 (t, 1H), 3.71 (dd, 1H), 3.35 (m, 1H). m.p. 118–120°.

EXAMPLE 2

(+/−)(E)7-Chloro-4-Phenylcarbamoylmethylene-1,2,3,4-Tetrahydro-Quinoline-2-Carboxylic Acid Sodium Salt Example 1 (0.019 g) was suspended in water and NaOH (0.1 N, 0.55 ml) was added with stirring. After 30 min the suspension was cooled to −40° and lyophilized for 24 hours. The title compound (15 mg) was isolated as a yellow solid.

$^1$H NMR: d (CDCl$_3$) 10.89 (bs, 1H), 7.70 (d, 2H), 7.30 (d, 1H), 7.27 (t, 2H), 6.99 (t, 1H), 6.77 (d, 1H), 6.42 (dd, 1H), 6.37 (bs, 1H), 6.25 (s, 1H), 3.25–3.42 (m, 2H), 2.69 (m, 1H).

IR: (nujol) n$_{max}$ (cm$^{-1}$) 3180–3500, 1651, 1599

EXAMPLE 3

(+/−)(E)5,7-Dichloro-4-Phenylcarbamoylmethylene-1,2,3,4-Tetrahydro-Quinoline-2-Carboxylic Acid To the stirred solution of intermediate 11 (0.016 g) in 4/1 EtOH/H$_2$O (2 ml) LiOH*H2O (0.003 g) was added. Stirring was continued at room temperature for 30 min. After concentratin the solution to approximately 0.5 ml, HCl (3 N, 5 ml) was added and the precipitate thus formed filtered, washed with small amounts of cold water and dried under vacuum to give the title compound (0.008 g) as a pale yellow solid.

$^1$H-NMR (DMSO): 12.71 (1H, s); 10.13 (1H, s); 7.63 (2H, d); 7.29 (2H, t); 7.03 (1H, t); 6.70 (1H, s); 6.69 (1H, m); 6.68 (1H, m); 4.12 (1H, t); 3.90 (1H, dd); 3.64 (1H, dd).

I.R.: (nujol): 3377 cm$^{-1}$, 3200–3600 cm$^{-1}$, 1726 cm$^{-1}$

EXAMPLE 4

(+/−)(E)5,7-Dichloro-4-Phenylcarbamoylmethylene-1,2,3,4-Tetrahydro-Quinoline-2-Carboxylic Acid Sodium Salt Example 3 (0.019 g) was suspended in water and NaOH (0.1 N, 1.06 ml) was added with stirring. After 30 min the suspension was cooled to −40° and lyophilized for 24 hours. The title compound (41 mg) was isolated as a yellow solid.

$^1$H-NMR(DMSO): 11.37 (s, 1H); 7.74 (d, 2H); 7.28 (m, 2H); 7.00 (m, 2H); 6.73 (d, 1H), 6.71 (m, 1H); 6.52 (s, 1H); 6.49 (d, 1H); 3.49 (m, 1H); 3.28 (m, 1H); 2.64 (m, 1H)

EXAMPLE 5

(+/−)(E)-4-(4-Acetylamino-Phenylcarbamoylmethylene)-5,7-Dichloro-1,2,3,4-Tetrahydro-Quinoline-2-Carboxylic Acid Intermediate 18 (0.027 g) was dissolved in a 2/1 mixture of EtOH and water (5 ml) and LiOH monohydrate (0.009 g) was added. The suspension was stirred and warmed to 60° for 40 min. After cooling the solution was acidified with 2 N HCl (2 ml) giving the title compound as a light yellow solid (0.016 g) after filtration.

$^1$H NMR (DMSO): 10.71 (bs, 1H); 10.08 (s, 1H); 9.86 (s, 1H); 7.54 (d, 2H); 7.48 (d, 2H); 7.10 (d, 1H); 6.69 (d, 1H); 6.67 (m, 2H); 4.10 (dt, 1H); 3.88 (dd, 1H); 3.05 (dd, 1H); 2.0 (s, 3H). m.p. 185° C.

EXAMPLE 6

(+/−)(E)-4-(3-Acetylamino-Phenylcarbamoylmethylene)-5,7-Dichloro-1,2,3,4-Tetrahydro-Quinoline-2-Carboxylic Acid Intermediate 19 (0.045 g) was suspended in ethanol (5 ml) and water (2.5 ml). To this solution, LiOH(H$_2$O) (0.007 g) was added and the reaction mixture was stirred for 1 h at 50° until a clear pale yellow solution was obtained. HCl 2 N (5 ml) was then added dropwise and the resulting acidic solution diluted with water (30 ml); the precipitate thus formed was filtered, washed with small amounts of cold water and dried to give the title compound (0.013 g) as a yellow solid.

$^1$H NMR (DMSO): 12.74 (bs, 1H); 10.15 (s, 1H); 9.94 (s, 1H); 7.97 (s, 1H); 7.31 (d, 1H); 7.29 (d, 1H); 7.12 (d, 1H); 6.72 (bs, 1H); 6.69 (d, 1H); 6.68 (d, 1H); 4.12 (m, 1H); 3.9 (m, 1H); 3.06 (m, 1H); 2.02 (s, 3H). m.p.: 190–193° C. m.p. 215° C.

EXAMPLE 7

(+/−)(E)-5,7-Dichloro-4-[3-(Chloro)Phenylcarbamoylmethylene]-1,2,3,4-Tetrahydro-Quinoline-2-Carboxylic Acid Intermediate 20 (0.02 g) was suspended in EtOH/H$_2$O (2/1), then LiOH*H$_2$O (5 mg) was added and the reaction was stirred at room temperature for 30 min. The solution was acidified with HCl 2 N and then extracted with EA, the organic layer was washed with water, dried and the solvent was removed under vacuum. The solid was suspended in water and filtered to give the title compound (0.013 g) as a yellow solid.

$^1$H-NMR (DMSO): 12.73 (bs, 1H); 10.35 (bs, 1H); 7.69 (t, 1H); 7.46 (m, 1H); 7.33 (m, 1H); 7.10 (m, 1H); 7.16 (m, 1H); 6.71 (d, 1H); 6.69 (d, 1H); 6.69 (bs, 1H); 4.13 (m, 1H); 3.89 (m, 1H); 3.02 (m, 1H)

I.R.(Nujol): 3402 cm$^{-1}$; 1718 cm$^{-1}$; 1659 cm$^{-1}$

EXAMPLE 8

(+/−)(E)-4-(4-Amino-Phenylcarbamoylmethylene)-5,7-Dichloro-1,2,3,4-Tetrahydro-Quinoline-2-Carboxylic Acid Intermediate 21 (0.110 g) was dissolved in a 1/1 mixture of EtOH and water (3 ml) and LiOH monohydrate (0.058 g) was added. The suspension was stirred at RT for 2 hrs. The solution was acidified with 2 N HCl giving the title compound as a light yellow solid (0.060 g) after filtration.

$^1$H NMR (DMSO): 12.60 (bm, 1H); 9.79 (bs, 1H); 7.33 (d, 2H); 7.07 (bm, 1H); 6.85–6.5 (m, 4H); 4.10 (m, 1H); 3.86 (dd, 1H); 3.09 (dd, 1H). m.p. >250° C.

EXAMPLE 9

(+/−)(E)-5,7-Dichloro-4-[4(Ureidomethyl)Phenylcarbamoylmethylene]-1,2,3,4-Tetrahydro-Quinoline-2-Carboxylic Acid Intermediate 26 (0.14 g) was suspended in EtOH/H$_2$O (2/1), then LiOH*H$_2$O (44 mg) was added and the reaction was stirred at room temperature for 1 hour. The solution was concentrated, diluited with water and acidified with HCl 2 N. The precipitate obtained was filtered and washed with water to give the title compound (0.084 g) as a yellow solid.

$^1$H-NMR (DMSO): 12.71 (bs, 1H); 10.11 (bs, 1H); 7.57 (d, 2H); 7.17 (d, 2H); 7.11 (bs, 1H); 6.7 (m, 3H); 6.34 (t, 1H); 5.48 (bs, 2H); 4.11 (d, 2H); 4.12 (m, 1H); 3.88 (dd, 1H); 3.07 (dd, 1H)

I.R.(Nujol): 3474, 3418, 3287 cm$^{-1}$; 1728 cm$^{-1}$; 1664 cm$^{-1}$; 1641 cm$^{-1}$; 1620 cm$^{-1}$ m.p.>.230° C.

EXAMPLE 10

(+/−)(E)-5,7-Dichloro-4-[4(Formylaminomethyl)Phenylcarbomoylmethylene]-1,2,3,4-Tetrahydro-Quinoline-2-Carboxylic Acid Intermediate 27 (0.050 g) was suspended in EtOH/H$_2$O (2/1), then LiOH*H$_2$O (14.6 mg) was added and the reaction was stirred at room temperature for 2 hours. The solution was concentrated, diluited with water and acidified with HCl 1 N. The precipitate obtained was filtered and washed with water to give the title compound (0.040 g) as a yellow solid.

$^1$H-NMR (DMSO): 12.73 (bs, 1H); 10.15 (s, 1H); 8.44 (t, 1H); 8.10 (d, 1H); 7.58 (d, 2H); 7.18 (d, 2H); 7.11 (d, 1H); 6.70–6.66 (m, 3H); 4.83 (d, 2H); 4.10 (m, 1H); 3.86 (dd, 1H); 3.06 (dd, 1H) I.R.(Nujol): 3406 cm$^{-1}$; 3344 cm$^{-1}$; 1720 cm$^{-1}$

EXAMPLE 11

(+/−)(E)-5,7-Dichloro-4-[4(Acetylaminomethyl)Phenylcarbomoylmethylene]-1,2,3,4-Tetrahydro-Quinoline-2-Carboxylic Acid Intermediate 28 (0.045 g) was suspended in EtOH/H$_2$O (3/1), then LiOH*H$_2$O (14 mg) was added and the reaction was stirred at room temperature for 45 min. The solution was concentrated, diluted with water and acidified with HCl 2 N. The precipitate obtained was filtered and washed with water to give the title compound (0.035 g) as a white solid.

$^1$H-NMR (DMSO): 12.73 (bs, 1H); 10.1 (s, 1H); 8.27 (t, 1H); 7.57 (d, 2H); 7.17 (d, 2H); 7.11 (d, 1H); 6.72–6.68 (m, 3H); 4.18 (d, 2H); 4.12 (m, 1H); 3.87 (dd, 1H); 3.06 (dd, 1H); 1.84 (s, 3H)

I.R.(Nujol): 3422–3265 cm$^{-1}$; 2725–2671 cm$^{-1}$; 1730 cm$^{-1}$; 1655 cm$^{-1}$

EXAMPLE 12

(+/−)(E)-5,7-Dichloro-4-[4(Isobutyrylamino) Phenylcarbomoylmethylene]-1,2,3,4-Tetrahydro-Quinoline-2-Carboxylic Acid Intermediate 29 (0.040 g) was suspended in EtOH/H$_2$O (1/1), then LiOH*H$_2$O (12 mg) was added and the reaction was stirred at room temperature for 1.5 hours. The solution was concentrated, diluted with water and acidified with HCl 1 N. The precipitate obtained was filtered and washed with water to give the title compound (0.030 g) as a white solid.

$^1$H-NMR (DMSO): 12.72 (bs, 1H); 10.11 (s, 1H); 9.75 (s, 1H); 7.53 (dd, 2H); 7.09 (s, 1H); 6.70–6.66 (m, 3H); 4.09 (bs, 1H); 3.86 (m, 1H); 3.06 (dd, 1H); 2.54 (m, 1H); 1.07 (d, 6H)

I.R.(Nujol): 3298 cm$^{-1}$; 1720 cm$^{-1}$; 1661 cm$^{-1}$ m.p. 230° C.

EXAMPLE 13

(+/−)(E)-5,7-Dichloro-4-[4(Isobutyrylaminomethyl) Phenylcarbamoylmethylene-1,2,3,4-Tetrahydro-Quinoline-2-Carboxylic Acid Intermediate 30 (0.89 g) was suspended in EtOH/H$_2$O (2/1), then LiOH*H$_2$O (26.4 mg) was added and the reaction was stirred at room temperature for 1 hour. The solution was acidified with HCl 2 N and then extracted with EA, the organic layer was washed with water, dried and the solvent was removed under vacuum. The solid was suspended in EA then petroleum ether was added and the solid was filtered to give the title compound (0.06 g) as a yellow solid.

$^1$H-NMR (DMSO): 12.71 (bs, 1H); 10.11 (s, 1H); 8.19 (t, 1H); 7.66 (d, 2H); 7.15 (d, 1H); 7.11 (m, 1H); 6.69 (d, 1H); 6.68 (bs, 1H); 6.67 (d, 1H); 4.18 (d, 2H); 4.11 (td, 1H); 3.88 (dd, 1H); 3.85 (dd, 1H); 2.39 (m, 1H); 1.01 (d, 6H)

I.R.(Nujol): 3302 cm$^{-1}$; 1726 cm$^{-1}$; 1653 cm$^{-1}$; 1628 cm$^{-1}$

EXAMPLE 14

(+/−)(E)-5,7-Dichloro-4-(4-Morpholin-4-Ylmethyl-Phenylcarbamoylmethylene)-1,2,3,4-Tetrahydro-Quinoline-2-Carboxylic Acid To a stirred solution of intermediate 31 (0.06 g) in ethanol/water (6 ml/2 ml), was added lithium hydroxide monohydrate (0.018 g) and the reaction mixture was stirred for 1 hrs. The solution was evaporated, then diluted with a saturated solution of ammonium chloride (20 ml) and extracted with ethyl acetate (2×30 ml), dried and concentrated in vacuum. The crude product was triturated in dichloromethane/diethyl ether (1.5 ml/3 ml) to give the title compound (0.04 g).

1H-NMR(DMSO): 11.0 (bs, 1H), 7.65 (d, 2H), 7.20 (d, 2H), 6.80 (bs, 1H), 6.73 (d, 1H), 6.57 (s, 1H), 6.54 (d, 1H), 3.54 (t, 4H)., 3.38 (s, 2H), 2.9 (m, 1H), 2.31 (m, 4H).

EXAMPLE 15

(+/−)(E)-4-(4-Carboxymethyl-Phenylcarbamoylmethylene)-5,7-Dichloro-1,2,3,4-Tetrahydro-Quinoline-2-Carboxylic Acid Intermediate 32 (0.083 g) was suspended in ethanol (12 ml) and water (4 ml). To this solution LiOH. (H$_2$O) (0.039 g) was added and the reaction mixture was stirred for 2 h 30 min at room temperature until a clear pale yellow solution was obtained. After evaporation of the solvent, HCl 1 N was then added dropwise until pH=1 and the resulting acidic solution diluted with water (15 ml); the precipitate thus formed was filtered, washed with small amounts of cold water and crystallized from EA/CH (4/2) to give the title compound (0.053 g) as a yellow solid.

$^1$H NMR (DMSO): 12.66 (s, 1H); 12.30 (s, 1H); 10.13 (s, 1H); 7.56 (d, 2H); 7.17 (d, 2H); 7.11 (d, 1H); 6.7–6.66 (m, 3H), 4.11 (m, 1H); 3.89 (dd, 1H); 3.49 (s, 2H); 3.04 (dd, 1H).

IR (nujol): 3368, 3180–3123, 1715, 1691. m.p. >220° C.

EXAMPLE 16

(+/−)(E)-5,7-Dichloro-4-(4-Carbamoylmethyl-Phenylcarbamoylmethylene)-1,2,3,4-Tetrahydro-Quinoline-2-Carboxylic Acid Intermediate 33 (0.150 g) was dissolved in tetrahydrofuran (5 ml), ethanol (20 ml) and water (10 ml). To this solution, LiOH(H$_2$O) (0.023 g) was added and the reaction mixture was stirred for 15' at room temperature. HCl 2 N (5 ml) was then added dropwise and the resulting acidic solution diluted with water (30 ml); the precipitate thus formed was filtered, washed with small amounts of cold water and dried to give the title compound (0.041 g) as a yellow solid.

$^1$H NMR (DMSO): 12.70 (s, 1H); 10.10 (s, 1H); 7.55–7.39 (d+s, 3H); 7.17–7.10 (d, 3H); 6.83–6.67 (m, 4H); 4.11–3.90 (m, 2H); 3.28 (s, 2H); 3.05 (dd, 1H).

EXAMPLE 17

(+/−)( E)-5,7-Dichloro-4-[4-(2-Isobutyrylamino-Ethyl)Phenylcarbamoylmethylene]-1,2,3,4-Tetrahydro-Quinoline-2-Carboxylic Acid Intermediate 34 (0.120 g) was suspended in ethanol (20 ml) and water (6 ml). To this solution LiOH(H$_2$O) (0.017 g) was added and the reaction mixture was stirred for 2 h at room temperature until a clear pale yellow solution was obtained. HCl 2 N (5 ml) was then added dropwise and the resulting acidic solution diluted with water (30 ml); the precipitate thus formed was filtered, washed with small amounts of cold water and dried to give the title compound (0.045 g) as a yellow solid.

$^1$H NMR (DMSO): 12.71 (s, 1H); 10.08 (s, 1H); 7.75 (t, 1H); 7.54 (d, 2H); 7.12 (d+s, 3H); 6.68 (m, 3H); 4.11 (m, 1H); 3.89 (dd, 1H); 3.21 (m, 2H); 3.04 (dd, 1H); 2.63 (t, 2H); 2.3 (m, 1H); 0.95 (d, 6H). m.p.: 216–218° C.

EXAMPLE 18

(+/−)(E)-5,7-Dichloro-4-[4-(2-Acetylamino-Ethyl) Phenylcarbamoylmethylene]-1,2,3,4-Tetrahydro-Quinoline-2-Carboxylic Acid Intermediate 35 (0.100 g) was suspended in ethanol (20 ml) and water (7 ml). To this solution, LiOH(H$_2$O) (0.033 g) was added and the reaction mixture was stirred for 2 h at room temperature until a clear pale yellow solution was obtained. HCl 1 N (5 ml) was then added dropwise and the resulting acidic solution diluted with water (30 ml); the precipitate thus formed was filtered, washed with small amounts of cold water and dried to give the title compound (0.054 g) as a yellow solid.

$^1$H NMR (DMSO): 12.71 (s, 1H); 10.13 (bs, 1H); 7.86 (t, 1H); 7.55 (d. 2H); 7.12 (d, 2H); 7.11 (bs, 2H); 6.98 (d, 1H); 6.70 (d, 1H); 6.70 (d, 1H); 6.67 (s, 1H); 4.1 (m, 1H); 3.9 (m, 1H); 3.2 (m, 1H); 3.09 (m, 1H); 1.76 (s, 3H). m.p.: 254–256° C.

IR (nujol): 3395, 3339, 1653

EXAMPLE 19

(+/−)(E)-5,7-Dichloro-4-[4-(3-Methyl-Butyrylamino)-Phenylcarbamoylmethylene]-1,2,3,4-Tetrahydro-Quinoline-2-Carboxylic Acid To a stirred solution of intermediate 38 (0.043 g) in ethanol/water (6 ml/2 ml), was added lithium hydroxide monohydrate (0.012 g) and the reaction mixture was stirred for 1½ hrs. The solution was evaporated, then diluted with a 3 N solution of hydrochloric acid (5 ml) and extracted with ethyl acetate (30 ml). The organic layer was dried and concentrated in vacuum. The crude product was triturated in ethyl acetate/diethyl ether (1 ml/5 ml) to give the title compound (0.02 g).

1H-NMR(DMSO): 12.72 (bs, 1H), 10.10 (bs, 1H), 9.78 (s, 1H), 7.55 (d, 2H), 7.50 (d, 2H), 7.10 (d, 1H), 6.70 (d, 1H), 6.67 (s, 1H), 6.67 (d, 1H), 4.10 (m, 1H), 3.86 (m, 1H)., 3.07 (m, 1H), 2.14 (d, 2H), 2.05 (m, 1H), 0.91 (d, 6H).

EXAMPLE 20

(+/−)(E)-4-(4-Acetylamino-Phenylcarbamoylmethylene)-5,7-Dichloro-1,2,3,4-Tetrahydro-Quinoline-2-Carboxylic Acid Sodium Salt Example 5 (0.050 g) was suspended in water (5 ml). NaOH 1 M was then added (0.115 ml) and the raction mixture was stirred for 0.5 h at room temperature until a clear pale yellow solution was obtained. The resulting solution was then freeze-dried for 48 h to give the title compound (0.027 g) as a yellow solid.

$^1$ H NMR (DMSO): 11.21 (bs, 1H); 9.86 (bs, 1H); 7.64 (d, 2H); 7.47 (d, 2H); 6.74 (d, 1H); 6.68 (d, 1H); 6.52 (m, 1H); 6.50 (d, 1H); 3.49 (m, 1H); 3.34 (m, 1H); 2.60 (m, 1H); 2.00 (s, 3H).

IR (nujol): 3398, 2720, 1657, 1600.

EXAMPLE 21

(+/−)-(E)-5,7-Dibromo-4-Phenylcarbamoylmethylene-1,2,3,4-Tetrahydroquinoline-2-Carboxylic Acid Intermediate 43 (0.042 g) was dissolved in 4/1 EtOH/H$_2$O (2 ml) and to the stirred solution LiOH*H2O (0.006 g) was added. Stirring was continued at room temperature for 30 min. After concentration the solution 0.5 ml, HCl (3 N, 5 ml) was added and the precipitate thus formed filtered, washed with small amounts of cold water and dried under vacuum to give the title compound (0.025 g) as a pale yellow solid.

$^1$H-NMR (DMSO): 12.71 (1H, s); 10.15 (1H, s); 7.65 (2H, d); 7.30 (2H, t); 7.06 (1H, t); 6.95 (1H, s); 6.68 (1H, m); 4.11 (1H, t); 3.90 (1H, dd); 3.03 (1H, m).

I.R.: (nujol): 3362 cm$^{-1}$, 3292 cm$^{-1}$, 1720 cm$^{-1}$, 1597 cm$^{-1}$ m.p.: (°C.): 115–120° C.

PHARMACY EXAMPLE

| Intravenous Infusion | % w/v |
|---|---|
| A glycine antagonist of formula (I) | 0.3–0.5 |
| Polysorbate 80 | 1 |
| tris(hydroxymethyl)aminomethane | 0.54 |
| Dextrose solution 5% w/v | qs to volume |

The glycine anatgonist and Polysorbate were added to a solution of tris(hydroxymethyl)aminomethane in a 5% aqueous dextrose solution suitable for injection. The solution was filtered through a sterile 0.2 micron sterlising filter and filled in containers before being sterilised by autoclaving.

The affinity of a compound of the invention for strychnine insensitive glycine binding site located on the NMDA receptor complex was determined using the procedure of Kishimoto H. et al J. Neurochem 1981, 37, 1015–1024. The pKi values obtained with representative compounds of the invention are given in the following table.

| Example No. | pKi |
|---|---|
| 2 | 7.4 |
| 4 | 8.2 |
| 5 | 8.1 |
| 6 | 7.8 |
| 7 | 7.4 |
| 8 | 7.8 |
| 9 | 8.4 |
| 10 | 8.3 |
| 11 | 8.3 |
| 12 | 7.8 |
| 13 | 7.8 |
| 14 | 8.1 |
| 15 | 7.72 |
| 16 | 8.18 |
| 17 | 7.9 |
| 18 | 7.9 |
| 19 | 7.73 |
| 21 | 7.58 |

The ability of compounds of the invention to inhibit NMDA induced convulsions in the mouse was determined using the procedure of Chiamulera C et al. Psychopharmacology 1990, 102, 551–552. In this test the ability of the compound when administered iv to inhibit the generalized seizures induced by an intracerebroventricular injection of NMDA in mice was examined at a number of dose levels.

From these results the dose required to protect 50% of the animals from the convulsive action of the NMDA was calculated. This expressed as mg/kg is referred to as the ED$_{50}$ value and results for representative compounds are given below:

| Ex No. | ED$_{50}$ mg/kg |
|---|---|
| 2 | 0.2 |
| 4 | 1 |
| 5 | 0.2 |

No untoward effects have been observed when compounds of the invention have been administered to mice (either i.v. or po) at pharmacologically active doses.

We claim:
1. A compound of formula (I)

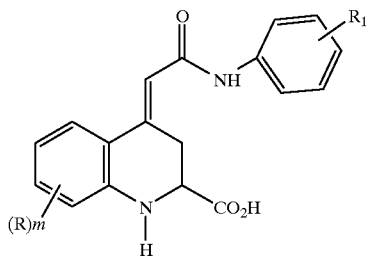

or a salt, or metabolically labile ester thereof wherein R represents a group selected from halogen, alkyl, alkoxy, amino, alkylamino, dialkylamino, hydroxy, trifluoromethyl, trifluoromethoxy, nitro, cyano, $SO_2R_2$ or $COR_2$ wherein $R_2$ represents hydroxy, methoxy, amino, alkylamino or dialkylamino; m is zero or an integer 1 or 2;

$R_1$ represents hydrogen, alkyl, alkoxy, nitro, trifluoromethyl, halogen or $(CH_2)_nR_3$ wherein $R_3$ is hydroxy, $COR_4$, $NR_5R_6$, $NHCOR_7$, or $NHCONR_8R_9$ group;

$R_4$ represents an alkoxy, amino or hydroxyl group;

$R_5$ and $R_6$ each independently represent hydrogen or alkyl group or $R_5$ and $R_6$ together with the nitrogen atom to which they are attached represent a heterocyclic group;

$R_7$ represents a hydrogen atom or optionally substituted alkyl, alkoxy, aryl or heterocyclic group;

$R_8$ represents hydrogen or alkyl group;

$R_9$ represents hydrogen, optionally substituted alkyl, aryl, heterocyclic or cycloalkyl group;

n is zero or an integer from 1 to 4.

2. A compound as claimed in claim 1 wherein m is 1 or 2, and R is a halogen atom in the 5 and/or 7 position.

3. A compound as claimed in claim 1 wherein m is 2 and R is chlorine in the 5 and 7 position.

4. A compound as claimed in claim 1 wherein $R_1$ is hydrogen, chlorine, $(CH_2)nCOR_4$ wherein $R_4$ is hydroxyl or amino, $(CH_2)_nNR_5R_6$ wherein $R_5$ and $R_6$ are each hydrogen or $NR_5R_6$ represents a morpholino group, $(CH_2)nNHCOR_7$ wherein $R_7$ is hydrogen or $C_{1-4}$alkyl, $(CH_2)nNHCONH_2$ and n is zero, 1 or 2.

5. A compound as claimed in claim 4 wherein $R_1$ represents hydrogen, chlorine, carboxymethyl, carbamoylmethyl, amino, morpholinomethyl, $(CH_2)nNHCOR_7$ (wherein n is zero, 1 or 2 and $R_7$ is hydrogen, methyl isopropyl or isobutyl) or $CH_2NHCONH_2$.

6. (±) (E) 4-(4-acetylamino-phenylcarbamoylmethylene)-5,7-dichloro-1,2,3,4-tetrahydroquinoline-2-carboxylic acid or a physiologically acceptable salt thereof.

7. A compound selected from
(±) (E) 5,7-Dichloro-4-phenylcarbamoylmethylene-1,2,3,4-tetrahydro-quinoline-2-carboxylic acid,
(±) (E) 7-Chloro-4-phenylcarbamoylmethylene-1,2,3,4-tetrahydro-quinoline-2-carboxylic acid,
(±) (E) 5,7-Dibromo-4-phenylcarbamoylmethylene-1,2,3,4-tetrahydro-quinoline-2-carboxylic acid,
(±) (E) 4-(4-Amino-phenylcarbamoylmethylene)-5,7-dichloro-1,2,3,4-tetrahydro-quinoline-2-carboxylic acid,
(±) (E) 4-(3-Acetylamino-phenylcarbamoylmethylene)-5,7-dichloro-1,2,3,4-tetrahydro-quinoline-2-carboxylic acid,
(±) (E) 5,7-Dichloro-4-(4-isobutytrylamino-phenylcarbamoylmethylene)-1,2,3,4-tetrahydro-quinoline-2-carboxylic acid,
(±) (E) 5,7-Dichloro-4-[4-(3-methyl-butyrylamino)-phenylcarbamoylmethylene]-1,2,3,4-tetrahydro-quinoline-2-carboxylic acid
(±) (E) 5,7-Dichloro-4-(3chloro-phenylcarbamoylmethylene)-1,2,3,4-tetrahydro-quinoline-2-carboxylic acid,
(±) (E) 5,7-Dichloro-4-[4-(isobutyrylamino-methyl)-phenylcarbamoylmethylene]-1,2,3,4-tetrahydro-quinoline-2-carboxylic acid
(±) (E) 5,7-Dichloro-4-[4-(ureidomethyl)-phenylcarbamoylmethylene]-1,2,3,4-tetrahydro-quinoline-2-carboxylic acid,
(±) (E) 4-[4-(Acetylamino-methyl)-phenylcarbamoylmethylene]-5,7-dichloro-1,2,3,4-tetrahydro-quinoline-2-carboxylic acid,
(±) (E) 5,7-Dichloro-4-(4-formylaminomethyl-phenylcarbamoylmethylene)-1,2,3,4-tetrahydro-quinoline-2-carboxylic acid,
(±) (E) 5,7-Dichloro-4-(4-morpholin-4-ylmethyl-phenylcarbamoylmethylene)-1,2,3,4-tetrahydro-quinoline-2-carboxylic acid
(±) (E) 4-[4-(2-Acetylamino-ethyl)-phenylcarbamoylmethylene]-5,7-dichloro-1,2,3,4-tetrahydro-quinoline-2-carboxylic acid,
(±) (E) 5,7-Dichloro-4-[4-(2-isobutyrylamino-ethyl)-phenylcarbamoylmethylene]-1,2,3,4-tetrahydro-quinoline-2-carboxylic acid
(±) (E) 4-(4-Carbamoylmethyl-phenylcarbamoylmethylene)-5,7-dichloro-1,2,3,4-tetrahydro-quinoline-2-carboxylic acid,
(±) (E) 4-(4-Carboxymethyl-phenylcarbamoylmethylene)-5,7-dichloro-1,2,3,4-tetrahydro-quinoline-2-carboxylic acid, and physiologically acceptable salts thereof.

8. A pharmaceutical composition comprising a compound as claimed in claim 1 in admixture with one or more physiologically acceptable carriers or excipients.

9. A compound as claimed in claim 1 wherein $R_1$ represents hydrogen, alkyl, alkoxy, nitro, trifluoromethyl, halogen or $(CH_2)_nR_3$ wherein $R_3$ is hydroxy, $COR_4$, $NR_5R_6$, $NHCOR_7$, or $NHCONR_8R_9$ group;

$R_4$ represents an alkoxy, or hydroxyl group;

$R_5$ and $R_6$ each independently represent hydrogen or alkyl group or $R_5$ and $R_6$ together with the nitrogen atom to which they are attached represent a heterocyclic group;

$R_7$ represents an optionally substituted alkyl, alkoxy, aryl or heterocyclic group;

$R_8$ represents hydrogen or alkyl group;

$R_9$ represents hydrogen, optionally substituted alkyl, aryl, heterocyclic or cycloalkyl group; n is zero or an interger from 1 to 4.

10. A compound as claimed in claim 9 wherein m is 2 and R is chlorine at the 5 and 7 position and $R_1$ represents hydrogen, $(CH_2)nCOR_4$, $(CH_2)nNR_5R_6$, $CH_2)_nNHCOR_7$ or $(CH_2)_nNHCONH_2$, n is zero, 1 or 2, $R_4$ represents hydroxyl, $R_5$ and $R_6$ each represent hydrogen or $NR_5R_6$ represents morpholino, $R_7$ represents $C_{1-4}$alkyl.

11. A process for the preparation of a compound of claim 1 which comprises:
(a) cylizing a compound formula (II)

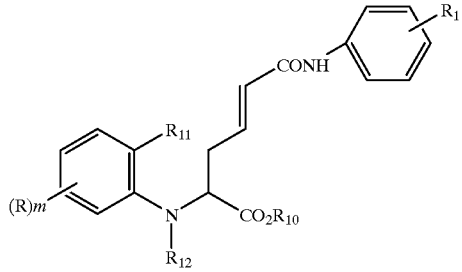

wherein R and m have the meanings defined in claim 1, $R_1$ has the meanings defined in claim 1 or is a protected derivative thereof, $R_{10}$ is a carboxyl protecting group, $R_{11}$ represents bromine or iodine and $R_{12}$ represents hydrogen or a nitrogen protecting group; or (b) reacting an activated derivative of the carboxylic acid of formula (III)

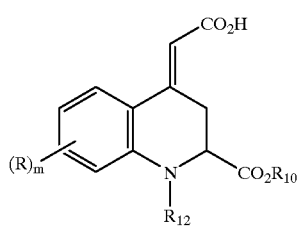

with an amine of formula (IV)

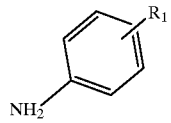

wherein R and m have the meanings defined in claim 1, $R_1$ has the meanings defined in claim 1 or is a protected derivative thereof, $R_{10}$ is a carboxyl protecting group, $R_{11}$ represents bromine or iodine and $R_{12}$ represents hydrogen or a nitrogen protecting group; or (c) for the preparation of compounds of formula (I) of claim 1 wherein $R_1$ is the group $(CH_2)_n NHCOR_7$ or $(CH_2)_n NHCONR_8 R_9$ and wherein n, $R_7$, $R_8$ and $R_9$ have the meanings defined in claim 1; by reacting a compound of formula (V)

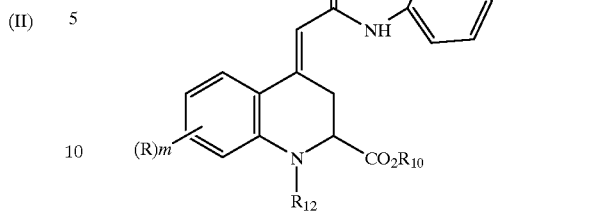

wherein R, m and n have the meanings defined in claim 1, $R_{10}$ is a carboxyl protecting group and $R_{12}$ is hydrogen or a nitrogen protecting group with an activated derivative of the acid $R_7 CO_2 H$ wherein $R_7$ has the meaning defined in claim 1 or is a protected derivative thereof; or a compound of formula (VI) or (VII)

wherein $R_8$ and $R_9$ have the meanings given in claim 1 for formula (I) or are protected derivatives thereof and $R_{13}$ is optionally substituted phenoxy, halogen or an imidazole group and removing any protecting group, where necessary in each of processes (a), (b) or (c).

12. A method of treatment of a mammal for a condition where antagonizing the effects of excitatory amino acids on the NMDA receptor complex is of therapeutic benefit comprising administration to a mammal in need thereof an effective amount of a compound as claimed in claim 1.

13. A method as claimed in claim 12 wherein the mammal is man.

14. A method according to claim 13 wherein the compound is (±) (E) 4-(4-acetylamino-phenylcarbamoylmethylene)-5,7-dichloro-1,2,3,4-tetrahydroquinoline-2-carboxylic acid or a physiologically acceptable salt thereof.

15. A method of claim 12 wherein the condition is neurotoxic damage or a neurodegenerative disease.

16. A method according to claim 15 wherein the compound is (±) (E) 4-(4-acetylamino-phenylcarbamoylmethylene)-5,7-dichloro-1,2,3,4-tetrahydroquinoline-2-carboxylic acid or a physiologically acceptable salt thereof.

* * * * *